United States Patent
He et al.

(10) Patent No.: US 8,462,341 B2
(45) Date of Patent: Jun. 11, 2013

(54) MOUNTING FOR DEVIATION ANGLE SELF COMPENSATING SUBSTANTIALLY ACHROMATIC RETARDER

(75) Inventors: Ping He, Lincoln, NE (US); Blaine D. Johs, Lincoln, NE (US); Steven E. Green, Lincoln, NE (US); Craig M. Herzinger, Lincoln, NE (US); Duane E. Meyer, Lincoln, NE (US); Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 162 days.

(21) Appl. No.: 13/065,090

(22) Filed: Mar. 14, 2011

(65) Prior Publication Data

US 2011/0188040 A1    Aug. 4, 2011

Related U.S. Application Data

(63) Continuation-in-part of application No. 12/290,787, filed on Nov. 4, 2008, now Pat. No. 7,907,280, and a continuation-in-part of application No. 11/633,138, filed on Dec. 4, 2006, now Pat. No. 7,450,231, and a continuation-in-part of application No. 11/590,408, filed on Oct. 31, 2006, now Pat. No. 7,460,230.

(60) Provisional application No. 60/733,910, filed on Nov. 4, 2005.

(51) Int. Cl.
*G01J 4/00* (2006.01)
(52) U.S. Cl.
USPC .. 356/365; 356/369; 359/486.01; 359/489.01

(58) Field of Classification Search
USPC .......................... 356/364–368; 359/494–496
See application file for complete search history.

(56) References Cited

U.S. PATENT DOCUMENTS

| | | | |
|---|---|---|---|
| 4,917,461 A | 4/1990 | Goldstein | 350/286 |
| 5,706,212 A | 1/1998 | Thompson et al. | 364/525 |
| 5,751,482 A | 5/1998 | Challender | |
| 5,963,325 A | 10/1999 | Johs et al. | 356/364 |
| 6,084,674 A | 7/2000 | Johs et al. | 356/364 |
| 6,084,675 A | 7/2000 | Herzinger et al. | 356/369 |
| 6,100,981 A | 8/2000 | Johs et al. | 356/364 |
| 6,118,537 A | 9/2000 | Johs et al. | 356/369 |
| 6,141,102 A | 10/2000 | Johs et al. | 356/364 |
| 6,353,477 B1 | 3/2002 | Johs et al. | 356/369 |
| 6,456,376 B1 | 9/2002 | Liphardt et al. | 356/369 |
| 7,233,396 B1 | 6/2007 | Hall et al. | 356/369 |
| 7,298,480 B2 | 11/2007 | Garcia-Caurel et al. | 356/364 |
| 7,450,231 B2 | 11/2008 | Johs et al. | 356/365 |
| 7,460,230 B2 | 12/2008 | Johs et al. | 356/365 |
| 2002/0181101 A1 | 12/2002 | Appel | |
| 2006/0023308 A1 | 2/2006 | Hunt | |

OTHER PUBLICATIONS

"Phase Retarders Highly Insensitive to Input Angle", Nagib, Applied Optics, vol. 77, No. 7, Mar. 1, 1998.
"Total Internal Reflection Phase Retarders Constructed for Prisms", Nagib, J. Opt. A : Pure Appl. Oct 6, 2004, 425-428.

*Primary Examiner* — Layla Lauchman
(74) *Attorney, Agent, or Firm* — James D. Welch

(57) ABSTRACT

A system, method of configuring, and application a system for introducing a relative phase retardation into orthogonally polarized components of an electromagnetic beam entered thereinto, wherein the system involves a substantially achromatic multiple element retarder system for use in wide spectral range (for example, 190-1700 nm) rotating compensator spectroscopic ellipsometer and/or polarimeter systems.

29 Claims, 12 Drawing Sheets

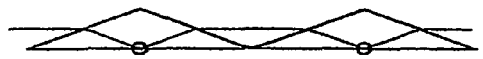
FIG. 9a
FIG. 10a
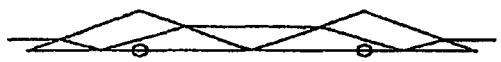
FIG. 9b
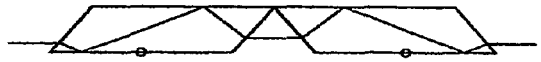
FIG. 10b
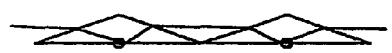
Beam angle=+1°, Ψ=56.953°, Δ=70.425°
FIG. 11a
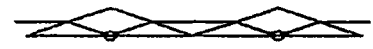
Beam angle=0°, Ψ=56.940°, Δ=70.419°
FIG. 11b
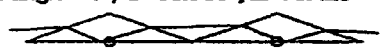
Beam angle=−1°, Ψ=56.953°, Δ=70.425°
FIG. 11c
Beam angle=+1°, Ψ=52.357°, Δ=114.232°
FIG. 11d
Beam angle=0°, Ψ=52.349°, Δ=114.221°
FIG. 11e
Beam angle=−1°, Ψ=52.357°, Δ=114.232°
FIG. 11f
FIG. 11
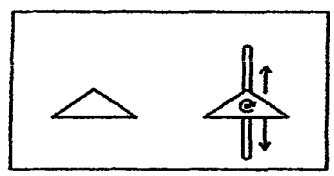
FIG. 12a
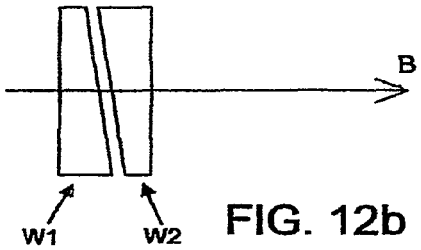
FIG. 12b

MOUNTING FOR DEVIATION ANGLE SELF COMPENSATING SUBSTANTIALLY ACHROMATIC RETARDER

This Application is a CIP of application Ser. No. 12/290,787 Filed Nov. 4, 2008 now U.S. Pat. No. 7,907,280; and therevia is a CIP of No. 11/633,138 Filed Dec. 4, 2006 now U.S. Pat. No. 7,450,231, and of No. 11/590,408 Filed Oct. 31, 2006 now U.S. Pat. No. 7,460,230, and therevia Claims Benefit of Provisional Application Ser. No. 60/733,910 Filed Nov. 4, 2005.

TECHNICAL FIELD

The present invention relates to retarders for entering retardance between orthogonal components of a beam of polarized electromagnetic radiation, and more particularly is a system for configuring and containing a system for introducing a relative phase retardation into orthogonally polarized components of an electromagnetic beam entered thereinto, wherein the system involves a substantially achromatic multiple element retarder system for use in wide spectral range (for example, 190-1700 nm) rotating compensator spectroscopic ellipsometer and/or polarimeter systems.

BACKGROUND

To obtain acceptable ellipsometer and/or polarimeter performance over a wide spectral range, compensator-based ellipsometer and/or polarimeter designs require a compensator element that provides retardance within a certain acceptable range over the entire spectral range. Traditionally, birefringent waveplates of quartz or $MgF_2$ have been used as compensator elements in rotating element designs. A single waveplate exhibits a (1/wavelength) dependence in retardance vs. wavelength, while a dual/multiple waveplate design, (as disclosed in U.S. Pat. No. 6,353,477), can minimize the effect of the (1/wavelength) dependence.

With the present invention in mind, known relevant patents are:
U.S. Pat. No. 5,706,212 to Thompson et al.;
U.S. Pat. No. 6,353,477 to Johs et al.;
U.S. Pat. No. 5,963,325 to Johs et al.;
U.S. Pat. No. 6,141,102 to Johs et al.;
U.S. Pat. No. 6,084,675 to Herzinger et al.;
U.S. Pat. No. 6,118,537 to Johs et al.;
U.S. Pat. No. 6,100,981 to Johs et al.;
U.S. Pat. No. 6,084,674 to Johs et al.

An Application which published Jun. 28, 2007 was recently identified and is US 2007/0146706 A1.

Further, references identified by the EPO in examination of an Application corresponding to the U.S. application Ser. No. 12/290,787 are:
"Total Internal Reflection Phase Retarders Constructed from Prisms", Nagib, J. Opt. A: Pure Appl., Opt 6 (2004), pp. 425-428;
"Phase Retarders Highly Insensitive to the Input Angle", Nagib, Applied Optics, Vol. 37, No. 7, March 1998;
U.S. Pat. No. 4,917,461, to Goldstein;
U.S. Pat. No. 6,456,376, to Liphardt et al.

While interesting, it is noted that the EPO has proceeded to allow Claims to prisms somewhat like disclosed in the Nagib articles, as application of said Nagib prisms failed to report any improvement in beam locus sensitivity to changes in prism translation. This is believed to be the result of the Nagib prisms having a length to width aspect ratio of over about 7.0. As disclosed in this Application, the presently Claimed Retarders have an aspect ratio of about 1.0. It is believed that the length of the prisms reported in the Nagib articles masked the beneficial effects achieved with present invention prisms.

Need remains for additional retarder systems which provide improved characteristics, and containment systems for securing them in intended positions, as well as protecting them from contamination for the environment.

DISCLOSURE OF THE INVENTION

First, as disclosed in Parent Applications, it is noted that the present invention can be applied in an ellipsometer or polarimeter system comprising:
a) a source of electromagnetic radiation;
b) a polarizer;
c) a stage for supporting a sample;
d) an analyzer; and
e) a detector;
said ellipsometer or polarimeter system further comprising at least one rotating or rotatable compensator system present at at least one location selected from the group consisting of:
between said source of electromagnetic radiation and said stage for supporting a sample; and
between said stage for supporting a sample and said detector.
The at least one rotating or rotatable compensator comprises at least two sequential elements oriented with respect to one another such that said entered electromagnetic beam undergoes internal reflection at least once in each of the elements, with the sequence, orientation, geometry, and symmetry of the elements being such that the locus of the output beam is substantially angularly undeviated from that of the input beam by a translation of the system, and the locus of the exiting output beam angle is substantially undeviated from that of the input beam by a rotation of the system about said beam locus.

It is noted that said ellipsometer or polarimeter system further comprising at least two rotating or rotatable compensator systems present at at least one location selected from the group consisting of:
both between said source of electromagnetic radiation and said stage for supporting a sample;
both between said stage for supporting a sample and said detector; and
one thereof being between said source of electromagnetic radiation and said stage for supporting a sample, and the other thereof being between said stage for supporting a sample and said detector.

The present invention is a system for introducing a relative phase retardation between orthogonal components of a polarized electromagnetic beam. Said system consists of at least two sequential elements, and said beam undergoes internal reflection at least once in each of said elements. Importantly, the sequence, orientation, geometry, and symmetry of the elements in the system is such that the locus of an exiting output beam is substantially angularly undeviated from that of the input beam by a translation of the system, and the exiting output beam angle is substantially angularly undeviated from that of the input beam by a rotation of the system about said beam locus.

One embodiment provides that two triangular shaped prisms comprise the elements. Preferred, non-limiting, design provides that the angles of said triangular prisms are 26, 128, and 26, and fabrication of the prisms can be, but is not necessarily, from fused silica.

Another embodiment provides that two parallelogram shaped rhombs are used for the elements. Preferred, non-limiting, design provides that angles of the parallelogram shaped rhombs are 36, 144, 36, and 144 degrees or 45, 135, 45 and 135 degrees, and again, fabrication of the parallelogram can be, but is not necessarily, from fused silica.

Another embodiment provides that four right angle prisms are used for elements. Preferred, non-limiting, design provides that angles are 45, 90 and 45, and again, fabrication of the prism can be, but is not necessarily, from fused silica.

Further, at least one of the elements can comprise a mechanism for translating and/or tilting at least one of the elements with respect to another element, for the purpose of aligning the elements of the system so as to reduce deviation between the locus of an output beam and that of a beam input to said system.

The present invention can be better described as being a system for introducing a relative phase retardation into orthogonally polarized components of an electromagnetic beam entered thereinto, said system consisting of at least two sequential elements oriented with respect to one another such that said entered electromagnetic beam undergoes internal reflection at least once in each of the at least two elements;
the sequence, orientation, geometry, and symmetry of the elements being such that the output beam position is substantially undeviated by a translation of the system, and the output beam angle is substantially undeviated by a rotation of the system about said beam locus.

The elements can be similar triangular shaped prisms each having:
first and second sides of equal length which project from one another at an angle greater than ninety degrees therebetween, and
a third side oriented opposite said greater than ninety degree angle,
said at least two similar triangular shaped prisms being oriented with respect to one another such that the third sides thereof are substantially colinear;
such that a beam of electromagnetic radiation caused to enter the first side of the first thereof, at a non-normal angle thereto, is refracted so that it internally reflects from said third side thereof, then exits said second side thereof in a direction such that it then enters the first side of another thereof at a non-normal angle thereto, is refracted so that it internally reflects from said third side thereof, then exits said second side thereof. The angles of the triangular prism can be 26, 128, and 26 degrees and the prisms can be fabricated from fused silica.

The elements can be parallelogram shaped rhombs, each said rhomb having first, second, third and forth sides, said first and third sides being substantially parallel to one another and said second and forth sides being substantially parallel to one another, said first and second, and said third and forth sides of the first parallelogram shaped rhomb meeting one another at angles greater than ninety degrees therebetween, and said second and third sides and said first and forth sides thereof meeting one another at angles less than ninety degrees therebetween with the second parallelogram shaped rhomb being positioned as a mirror image thereto,
said at least two parallelogram shaped rhombs being oriented with their second sides being substantially colinear and with their forth sides thereof being substantially colinear;
such that a beam of electromagnetic radiation caused to enter the first side of the first thereof, at a non-normal angle thereto, is refracted so that it internally reflects from said forth and second sides thereof, then exits said third side thereof in a direction such that it then enters the first side of the second thereof at a non-normal angle thereto, is refracted so that it internally reflects from said second and forth side thereof, then exits said third side thereof. The angles of the parallelogram shaped rhomb can be 36, 144, 36, and 144 degrees or 45, 135, 45 and 135 degrees, and can be fabricated from fused silica.

The elements can be rhombs, each said rhomb having first, second, third and forth sides, said first and third sides being substantially parallel to one another and said second and forth sides being substantially parallel to one another, said first and second, and said third and forth sides of the first rhomb meeting one another at angles greater than ninety degrees therebetween, and said second and third sides and said first and forth sides of the first rhomb meeting one another at angles less than ninety degrees therebetween, with the second rhomb appearing as a mirror image;
said at least two parallelogram shaped rhombs being oriented with their first and third sides being substantially parallel to one another;
such that a beam of electromagnetic radiation caused to enter the first side of the first thereof, at substantially a normal angle thereto, then proceeds so that it internally reflects from said forth and second side thereof, then exits said third side thereof in a direction such that it then enters the first side of another thereof at a substantial normal angle thereto, then proceeds so that it internally reflects from said second and forth side thereof, then exits said third side thereof;
said system being characterized in that at least one of the sides of at least one of the parallelogram shaped rhombs has a coating thereupon which has a different, (eg. lower), refractive index than does the material from which said corresponding parallelogram shaped rhomb is comprised. The angles of the parallelogram shaped rhomb can be 36, 144, 36, and 144 degrees or 45, 135, 45 and 135 degrees, and the rhombs can be fabricated from fused silica, with the coating being $MgF_2$.

The elements can be at least four sequential elements, said beam undergoing internal reflection once in each of the elements, said system being characterized in that each of said at least four elements are right angle prisms having right angle sides adjacent to the right angle thereof and a side opposite the right angle thereof; said right angle prisms being oriented with respect to one another such that, as viewed in side elevation, the first right angle prism is positioned so that its side opposite the right angle thereof is facing downward and to the right, and so that directly above the first right angle prism is present the second right angle prism, which is oriented so that its side opposite the right angle thereof is facing upward and to the left, and so that directly to the right of the second right angle prism is the third right angle prism, which is oriented so that its side opposite the right angle thereof is facing upward and to the right, and so that directly below the third right angle prism is positioned the forth right angle prism, oriented so that its side opposite the right angle thereof is facing downward and to the left. The angles of the right angle prisms can be 45, 90 and 45 degrees and the right angle prisms can be fabricated from fused silica.

As recited above, any of the foregoing embodiments can be further characterized by at least one selection from:
at least one of the sequential elements has a mechanism for translating and/or tilting the element, for the purpose of aligning the system such that the output beam is substantially undeviated from said input beam;
at least one of the sequential elements has a coating upon a surface thereof at which internal reflection of a beam of electromagnetic radiation occurs, said coating having a different refractive index than does the material from which said corresponding element is comprised;
at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge can be rotated with respect to another said wedge and/or both wedges can be rotated simultaneously, for the purpose of aligning the system such that the output beam is substantially undeviated from said input beam.

A present invention method involves providing a compensator system comprising at least two elements oriented with respect to one another such that an entered electromagnetic beam undergoes internal reflection at least once in each of the elements, with the sequence, orientation, geometry, and symmetry of the elements being such that the locus of output beam from said system is substantially undeviated from that of the input beam by a translation of the system, and the locus of the output beam angle is substantially undeviated from that of the input beam by a rotation of the system about said beam locus;

said method comprising the steps of:
a) providing a system for introducing a relative phase retardation into orthogonally polarized components of an electromagnetic beam, said system comprising of at least two sequential elements, said beam undergoing internal reflection at least once in each of the elements;
b) causing a beam of electromagnetic radiation to enter said system via a first of said at least two sequential elements and pass through said at least two sequential elements while undergoing at least one internal reflection in each;
such that the exiting beam has retardation entered thereinto via said internal reflections, and such that the locus of the exiting beam is substantially undeviated from that of the entering beam.

A coating can be provided on at least one surface of at least one of element, said coating having a refractive index less than or greater than that of the material from which said element is comprised.

Said method can further comprise providing an additional sequential multiple wedge system in said system, wherein one said wedge can be rotated with respect to another thereof and/or both wedges can be rotated simultaneously, for the purpose of aligning the system such that the output beam from said forth right angle prism is substantially undeviated from the beam input to said first right angle prism.

Continuing, the foregoing is particularly applicable to retarder systems wherein the at least two elements which are oriented with respect to one another are identical. It does happen, however, that in practice two parallelogram shaped elements will not be identical. When such non-identical elements are paired to form a retarder system, the result can be that angular deviation and/or lateral offset of a beam of electromagnetic radiation entered thereinto results by passage therethrough. To minimize such adverse effects it is disclosed that it is good practice to first pair up only well matched parallelogram shaped elements. In addition, when a system of two well matched parallelograms is constructed, it can still happen that a beam entered thereto will introduce a lateral offset into an exiting beam. Alignment practice can then involve rotating, as a whole, the system of two well matched parallelogram shaped elements which are fixed with respect to one another, so that the input beam enters at an angle offset from a normal to the side of the first parallelogram into which the beam of electromagnetic radiation is entered. This practiced can serve to overcome beam lateral translation.

The present invention is then a method of constructing a multiple element retarder system for introducing a relative phase retardation between orthogonal components of a polarized beam of electromagnetic radiation entered thereinto. Said multiple element retarder system comprises at least two similar elements which are sequentially secured with respect to one another such that a beam of electromagnetic radiation entered to the first thereof undergoes internal reflection at least once in each of the at least two elements, and exits the second thereof along a locus which is not angularly deviated or laterally offset from that of said entered beam by more than acceptable amounts.

Said method comprises the steps of:
practicing steps a and b in either order, said steps a and b being:
a) providing a multiplicity of similar elements;
b) defining acceptable beam angular deviation and lateral offset values.
Said method further comprises:
c) from said multiplicity of similar elements selecting two thereof and securing them in a sequential system, then experimentally monitoring angular deviation entered to a beam of electromagnetic radiation entered to a first thereof, so that it undergoes internal reflection at least once in each of the at least two elements, and then exits the second thereof;
d) determining if the beam angular deviation experimentally monitored in step c is acceptable under the criteria defined in step b, and performing a selection from the group consisting of:
 accepting the said sequential system if said defined angular deviation criteria is met and proceeding to step e; and
 rejecting said sequential system and repeating step c if said defined angular deviation criteria is not met.
Said method continues with:
e) if practice of step d results in accepting said sequential system, proceeding to determine if a lateral offset exists between the beam entered to the first element and that exiting the second element, and if so performing at least one selection from the group consisting of:
 changing the relative orientation of said selected elements with respect to one another; and
 rotating said system of the two selected elements as said unit about an axis not parallel to the electromagnetic beam;
until said lateral offset entered to said beam of electromagnetic radiation is determined to be acceptable under the criteria defined in step b.
Said method can further include:
f) optionally experimentally re-checking if the angular deviation entered to said beam of electromagnetic radiation is still acceptable after practice of step e; and
accepting said sequential system only if both the angular deviation and lateral offset entered to said beam of electromagnetic radiation are then acceptable under the criteria of step b.

Step c can comprise determining a plurality of acceptable sequential combinations of selected elements via a systematic testing of at least some of all possible sequential combinations of selected elements, followed by separate practice of steps d-f for at least two of said sequential combinations.

Step c can also involve selecting two sequential parallelogram shaped rhombs as elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween, Step a can involve providing two parallelogram shaped rhombs oriented with their first and third sides being substantially parallel to one another, wherein "substantially parallel to one another" means that said third (RS3) side of said first (RS1) and first (RS1) side of the second of said parallelogram shaped rhombs are offset from being parallel to one another by no more than about +/−ten (10) degrees;

such that a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof.

Step c can involve selecting two sequential parallelogram shaped rhombs wherein the angles of the parallelogram shaped rhomb are nominally selected from the group consisting of:

36, 144, 36, and 144 degrees; and
45, 135, 45 and 135 degrees.

Step c can involve selecting two sequential parallelogram shaped rhombs which are fabricated from fused silica.

Where two sequential parallelogram shaped rhombs are involved they can be characterized by at least one of the second RS2 and forth RS4 sides of at least one of the parallelogram shaped rhombs having a coating thereupon which has a different refractive index than does the material from which said corresponding parallelogram shaped rhomb is comprised.

Step a can involve providing a multiplicity of parallelogram shaped rhombs as elements and step b involves selecting two sequential parallelogram shaped rhombs as elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween, said two parallelogram shaped rhombs being oriented with their first and third sides being substantially parallel to one another, wherein "substantially parallel to one another" means that said third (RS3) side of said first and first (RS1) side of the second of said parallelogram shaped rhombs are parallel to one another within about +/−ten (10) degrees. In use a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially-normal angle thereto, then proceeds so that it internally reflects from said second RS2 parallelogram shaped rhomb and forth RS4 side thereof, then exits said third RS3 side thereof;

said system being characterized in that at least one of the second RS2 and forth RS4 sides of at least one of the parallelogram shaped rhombs has a coating thereupon which has a different refractive index than does the material from which said corresponding parallelogram shaped rhomb is comprised.

Said method can involve providing two sequential parallelogram shaped rhombs wherein the angles of the parallelogram shaped rhomb are nominally selected from the group consisting of:

36, 144, 36, and 144 degrees; and
45, 135, 45 and 135 degrees.

Said method can involve providing sequential parallelogram shaped rhombs which are fabricated from fused silica and the coating is $MgF_2$.

Step b can involve selecting a system of sequential elements which are further characterized by at least one selection made from the group consisting of:

at least one of the sequential elements is mounted to a mechanism for translating and/or tilting the element, for the purpose of aligning the system such that the output beam is substantially angularly undeviated from said input beam;

at least one of the sequential elements has a coating upon a surface thereof at which internal reflection of a beam of electromagnetic radiation occurs, said coating having a different refractive index than does the material from which said corresponding element is comprised;

at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge W1 can be rotated with respect to another W2 thereof and/or both wedges W1 W2 can be rotated simultaneously, for the purpose of aligning the system such that the output beam is substantially angularly undeviated from said input beam.

A more detailed method of constructing a multiple element retarder system for introducing a relative phase retardation between orthogonal components of a polarized beam of electromagnetic radiation entered thereinto, said multiple element retarder system comprising at least two similar elements which are sequentially secured with respect to one another such that a beam of electromagnetic radiation entered to the first thereof undergoes internal reflection at least once in each of the at least two elements, and exits the second thereof along a locus which is not angularly deviated or laterally offset from that of said entered beam by more than acceptable amounts; comprises, before practice of step d, the steps of:

a) providing a multiplicity of similar elements;
b) experimentally determining and recording data describing measured angular deviation entered to a beam of electromagnetic radiation by interaction with each of said multiplicity of similar elements individually;
c) defining acceptable beam angular deviation and laterally offset values and providing a computer program which is capable of analyzing said data recorded in step b.

Said method further comprises the steps of:

d) applying said computer program provided in step c to data recorded in step b the end that pairings of similar elements are identified which in sequence meet the acceptable beam angular deviation values identified in step c;

e) selecting at least one of said pairings of similar elements identified in step d and securing the paired similar elements in a sequential system, then experimentally monitoring angular deviation entered to a beam of electromagnetic radiation entered to a first thereof, so that it undergoes internal reflection at least once in each of the at least two elements, and then exits the second thereof;

f) determining if the beam angular deviation experimentally monitored in step e is acceptable under the criteria defined in step c, and performing a selection from the group consisting of:
  accepting the said sequential system if said defined angular deviation criteria is met and proceeding to step g; and
  rejecting said sequential system and repeating step e with another selected pairing of similar elements if said defined angular deviation criteria is not met;

g) if practice of step f results in accepting said sequential system, proceeding to determine if a laterally offset exists between the beam entered to the first element and that exiting the second element, and if so performing at least one selection from the group consisting of:
  changing the relative orientation of said selected elements with respect to one another; and
  rotating said system of the two selected elements as said unit about an axis not parallel to the beam of electromagnetic radiation;
until said lateral offset entered to said beam of electromagnetic radiation is determined to be acceptable under the criteria defined in step c.

Said method can optionally comprise:
h) optionally experimentally re-checking if the angular deviation entered to said beam of electromagnetic radiation is still acceptable after practice of step g.

Said method can also comprise:
i) said method further comprising:
  i1) providing a containment system with provision for receiving selected prisms thereinto in a desired relationship with respect to one another.
  i2) placing said selected prisms into said containment system.

And said method can further comprise said containment system being characterized by:
  an outer enclosure which separates an outer environment from the enclosed inner volume in which is present said provision for receiving selected prisms thereinto in a desired relationship with respect to one another therewithin;
  said outer enclosure further comprising means for flowing purging gas into and out of said enclosed inner volume such that the inner volume can be caused to contain a gas which is not damaging to the outer surfaces of said selected prisms caused to be present therein;
  in which said method further comprises:
  j) flowing a gas into said enclosed inner volume through said means for flowing purging gas into said enclosed inner volume, such that some amount thereof passes through said inner volume and out of said means for flowing gas out of said inner volume;
  k) optionally sealing said means for flowing purging gas into and out of said enclosed inner volume such that outside environment can not thereafter enter into said inner volume; to the end that the inner volume is caused to present said gas outer surfaces of said selected prisms caused to be present therein, continuously or for a period followed by sealing.

Practice of said method enables the ability to accept said sequential system only if both the angular deviation and lateral offset entered to said beam of electromagnetic radiation are then acceptable under the criteria of step c.

Said method can involve the elements being paired by said computer program in step d, because neither of them was experimentally determined to enter significant angular deviation to a beam of electromagnetic radiation in step b, or the elements being paired by said computer program in step d because each of them was experimentally determined to enter angular deviation to a beam of electromagnetic radiation in step b, but in an offsetting manner.

Said method can involve said similar elements each provide at least two sides, either of which can be oriented to serve as the side into which a beam of electromagnetic radiation is input, and in which the step b practice of experimentally determining and recording data describing measured angular deviation entered to a beam of electromagnetic radiation by each of said multiplicity of similar elements individually is performed for each such orientation, and in which all recorded data is considered in step e.

Said method can further comprise determining, and placing in order, the relatively best pairings of similar elements by a method selected from the group consisting of:
  using results from applying said computer program in step d to data recorded in step b to identify pairings of similar elements which in sequence provide the least beam angular deviation; and
  recording experimental data determined in step e and applying said data to identify pairings of similar elements which in sequence provide the least beam angular deviation;

Said method can optionally further comprise defining a cut-off criteria point as regards beam angular deviation, and rejecting pairings which do not meet said cut-off criteria.

Said method step a can involve providing parallelogram shaped rhombs and step e involves selecting two sequential parallelogram shaped rhombs as elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween,
said two parallelogram shaped rhombs being oriented with their first and third sides being substantially parallel to one another, wherein "substantially parallel to one another" means that said third (RS3) side of said first and first (RS1) side of the second of said parallelogram shaped rhombs are offset from being parallel to one another by no more than about +/−ten (10) degrees;
such that a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof.

Said method step c can involve selecting two sequential parallelogram shaped rhombs wherein the angles of the parallelogram shaped rhomb are nominally selected from the group consisting of:
  36, 144, 36, and 144 degrees; and
  45, 135, 45 and 135 degrees.

Said method can involve, in step c, selecting two sequential parallelogram shaped rhombs which are fabricated from fused silica.

Said method can involve selecting two sequential parallelogram shaped rhombs which are characterized by at least one of the second RS2 and forth RS4 sides of at least one of the parallelogram shaped rhombs having a coating thereupon which has a different refractive index than does the material from which said corresponding parallelogram shaped rhomb is comprised.

Said method step a can involve providing a multiplicity of parallelogram shaped rhombs as elements and step e involve selecting two sequential parallelogram shaped rhombs as elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween, said two parallelogram shaped rhombs being oriented with their first and third sides being substantially parallel to one another, wherein "substantially parallel to one another" means that said third (RS3) side of said first and first (RS1) side of the second of said parallelogram shaped rhombs are offset from being parallel to one another by no more than about +/−ten (10) degrees;

such that a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof;

said system being characterized in that at least one of the second RS2 and forth RS4 sides of at least one of the parallelogram shaped rhombs has a coating thereupon which has a different refractive index than does the material from which said corresponding parallelogram shaped rhomb is comprised.

Said method step a can involve providing two sequential parallelogram shaped rhombs wherein the angles of the parallelogram shaped rhomb are nominally selected from the group consisting of:

36, 144, 36, and 144 degrees; and
45, 135, 45 and 135 degrees.

Said method step a can involve providing sequential parallelogram shaped rhombs which are fabricated from fused silica and the coating is $MgF_2$.

Said method step e can involve selecting a system of sequential elements which are further characterized by at least one selection made from the group consisting of:

at least one of the sequential elements is mounted to a mechanism for translating and/or tilting the element, for the purpose of aligning the system such that the exiting beam is substantially angularly undeviated from said input beam;

at least one of the sequential elements has a coating upon a surface thereof at which internal reflection of a beam of electromagnetic radiation occurs, said coating having a different refractive index than does the material from which said corresponding element is comprised;

at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge W1 can be rotated with respect to another W2 thereof and/or both wedges W1 W2 can be rotated simultaneously, for the purpose of aligning the system such that the output beam is substantially angularly undeviated from said input beam.

Any of the foregoing methods can involve performing at least one selection from the group consisting of:

storing at least some data in machine readable media;

analyzing at least some of the data and storing at least some of the results of said analysis in machine readable media;

displaying at least some data by electronic and/or non-electronic means;

analyzing at least some of the data and displaying at least some of the results of said analysis by electronic and/or non-electronic means;

causing at least some data to produce a signal which is applied to provide a concrete and tangible result;

analyzing at least some of the data and causing at least some thereof to produce a signal which is applied to provide a concrete and tangible result.

Continuing, the present invention is further an ellipsometer or polarimeter system comprising:

a) a source of electromagnetic radiation;
b) a polarizer;
c) a stage for supporting a sample;
d) an analyzer; and
e) a detector;

wherein said ellipsometer or polarimeter system further comprises at least one rotating or rotatable compensator system present at at least one location selected from the group consisting of:

between said source of electromagnetic radiation and said stage for supporting a sample; and between said stage for supporting a sample and said detector.

The at least one rotating or rotatable compensator comprises at least two sequential elements oriented with respect to one another such that said entered electromagnetic beam undergoes internal reflection at least once in each of the elements, with the sequence, orientation, geometry, and symmetry of the elements being such that the locus of the output beam is substantially angularly undeviated from that of the input beam by a translation of the system, and the locus of the output beam angle is substantially undeviated from that of the input beam by a rotation of the system about said beam locus.

In particular, said at least one rotating or rotatable compensator can comprise two sequential parallelogram shaped rhombs as elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween, said two parallelogram shaped rhombs being oriented with their first and third sides being substantially parallel to one another, wherein "substantially parallel to one another", means that said third (RS3) side of said first and first (RS1) side of the second of said parallelogram shaped rhombs are parallel to one another within about +/−ten (10) degrees;

such that a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof.

The present invention will be better understood by reference to the Detailed Description Section of this Specification, in combination with reference to the Drawings.

BRIEF DESCRIPTION OF THE DRAWINGS

FIGS. 9a, 9b, 10a and 10b show that the most useful property of the new retarder design is that as the angle of the input beam is changed, the resulting transmitted bean angle does not change.

FIGS. 11a-11f show very small beam polarization change, in terms of PSI and DELTA, for a given change in beam angle.

FIG. 12a demonstrates translation and rotation capability for an element of a two sequential element retarder system.

FIG. 12b shows a two wedge system which allows for relative rotation therebetween.

DETAILED DISCLOSURE OF THE INVENTION

Figure 1:
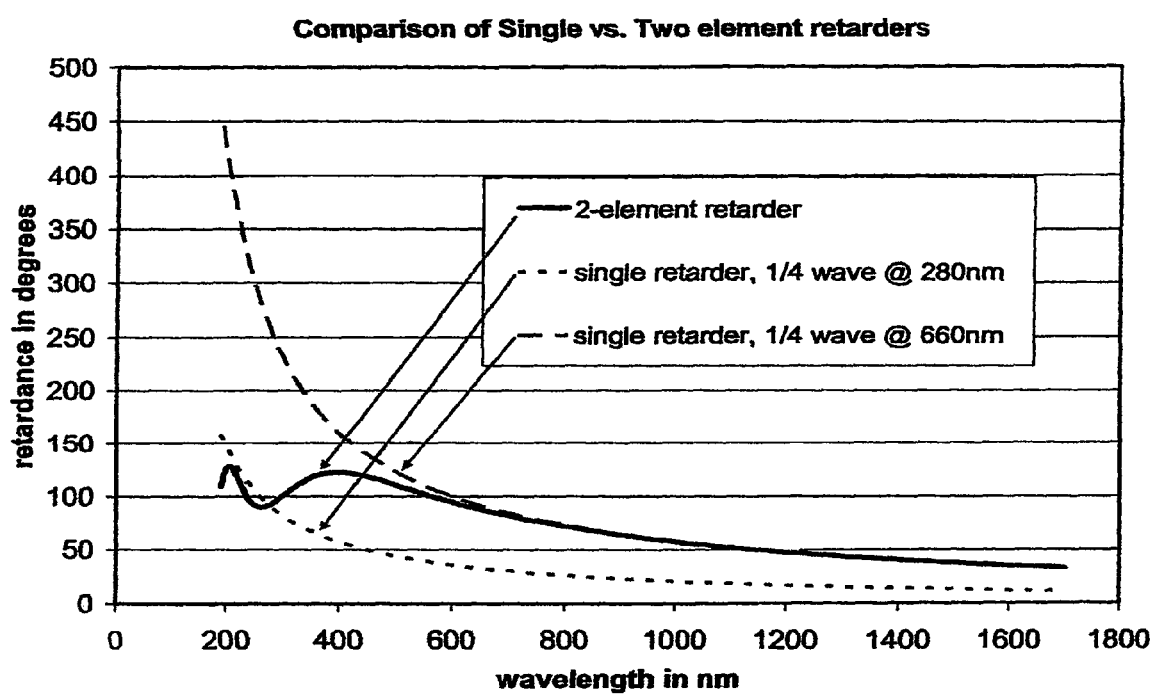
FIG. 1 shows retardence results from a retarder comprising two birefringent waveplates over a spectroscopic range.
Figure 2:
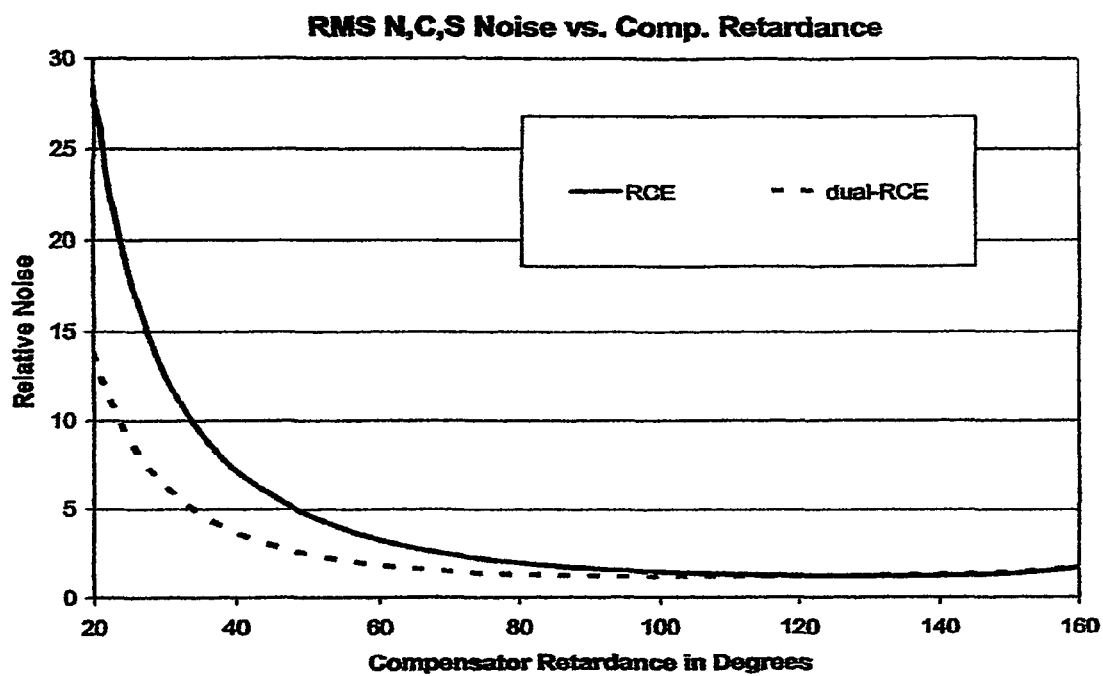
FIG. 2 shows the Root Mean Squared (RMS) noise in ellipsometric parameters N, C and S.

Turning now to FIG. 1, as introduction, results from a retarder comprising two birefringent waveplates are shown. Note that the retardence varies from 35-130 degrees over the typical UV-VIS-NIR spectral range of 190-1700 nm. FIG. 2 shows the Root Mean Squared (RMS) noise in the ellipsometric parameters;

$N=\cos(2\psi)$;
$C=\sin(2\psi)\cos(\Delta)$; and
$S=\sin(2\psi)\sin(\Delta)$;

for the rotating compensator ellipsometer (RCE) and dual rotating compensator ellipsometer (dual-RCE) configurations as a function of compensator retardence. See FIG. 13 for insight to the construction of a rotating compensator ellipsometer (RCE) with one or two of the shown Compensators (C), (C') (C") considered as present. Continuing, for said rotating compensator ellipsometer (RCE) configuration it is disclosed that it has been determined to be beneficial to keep the retardence between 80 and 160 degrees, as this keeps the relative RMS N,C,S noise to less than 2.0. In that regard the dual-RCE configuration is slightly more forgiving over the retardence range is 60-160 degrees. It should be appreciated that FIGS. 1 and 2 show that using birefringent waveplates through which a beam of electromagnetic radiation is caused to pass, in wide spectral range rotating compensator ellipsometer systems, compromises the noise performance of the system.

In view of the above disclosure, it is disclosed that an alternative approach to effecting retardence is by total internal reflection. FIGS. 3a and 3b show Generated (Gen) retardence vs. total internal reflection angle and wavelength, (at a given angle), for the fused silica/air interface. Note that the change in retardence vs. wavelength for total internal reflectance is very small compared to the retardence induced by the (1/wavelength) dependence of birefringence-induced retardence. Fresnel rhomb retarders which are based on this effect are readily available. However, a typical ¼ wave Fresnel rhomb design translates the beam significantly, and the retardence also changes significantly as a function of beam angle, making it impractical to use a Fresnel rhomb in a rotating compensator style ellipsometer or polarimeter design. FIG. 4a shows a Typical Wave ¼ wave 90 degree retardence Fresnel Rhomb and demonstrates the translation effect. FIG. 4b shows a known approach to combining two Fresnel Rhombs to achieve a substantially non-translated beam. The rhombs each have first (RS1), second (RS2), third (RS3) and forth (RS4) sides, said first (RS1) and third (RS3) sides being substantially parallel to one another, and said second (RS2) and forth (RS4) sides being substantially parallel to one another, said first (RS1) and second (RS2), and said third (RS3) and forth (RS4) sides of said first Fresnel Rhomb meeting one another at angles greater than ninety degrees therebetween, and said second (RS2) and third (RS3) sides and said first (RS1) and forth (RS4) sides thereof meeting one another at angles less than ninety degrees therebetween. Note that said at least two parallelogram shaped rhombs are oriented with their first (RS1) and third (RS3) sides being substantially parallel to one another. In use a beam of electromagnetic radiation caused to enter the first (RS1) side of the first Fresnel Rhomb, at a substantially normal angle thereto, then proceeds so that it internally reflects from said forth (RS4) and second (RS2) side thereof, then exits said third (RS3) side thereof in a direction such that it then enters the first (RS1) side of the second Fresnel Rhomb at a substantially normal angle thereto, then proceeds so that it internally reflects from said second (RS2) and forth (RS4) side thereof, then exits said third (RS3) side thereof. Said system is distinguished over known configurations in that it is characterized in that at least one of the sides (RS1) (RS2) (RS3) (RS4) of at least one of the parallelogram shaped rhombs has a coating thereupon which has a different refractive index than does the material from which said corresponding parallelogram shaped rhomb is comprised. Preferred practice is to coat sides (RS2) and (RS4) of each rhomb. The angles of the parallelogram shaped rhomb can be 36, 144, 36, and 144 degrees or 45, 135, 45 and 135 degrees, and the rhombs can be fabricated from fused silica, with the coating being a material, (eg. $MgF_2$), with a lower refractive index.

Figure 4C:
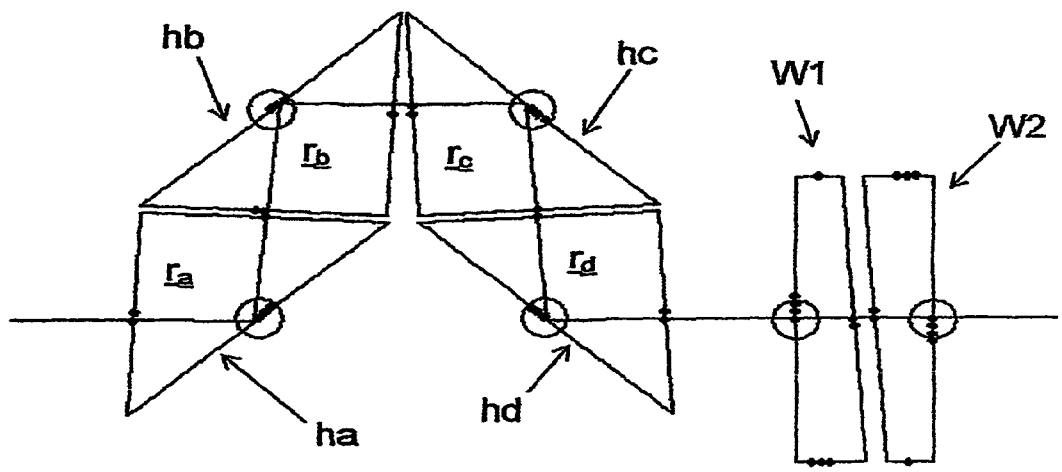
FIG. 4c shows a variation on the FIG. 4b system comprising four right angle prisms and optional wedge elements as also shown in FIG. 12b.
Figure 4A:
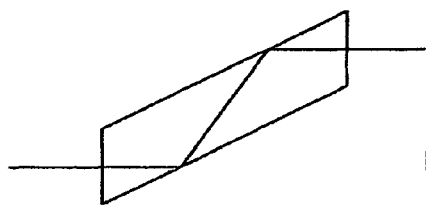
FIG. 4a shows a Typical ¼ Wave 90 degree retardence Fresnel Rhomb and demonstrates the translation effect.
Figure 4B:
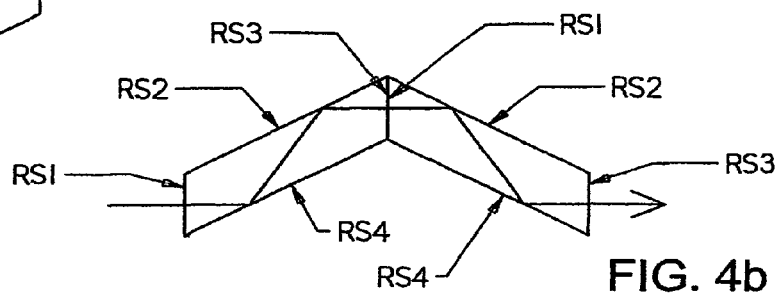
FIG. 4b shows how two Fresnel Rhombs can be combined to result in an angularly non-deviated beam.
Figure 4D:
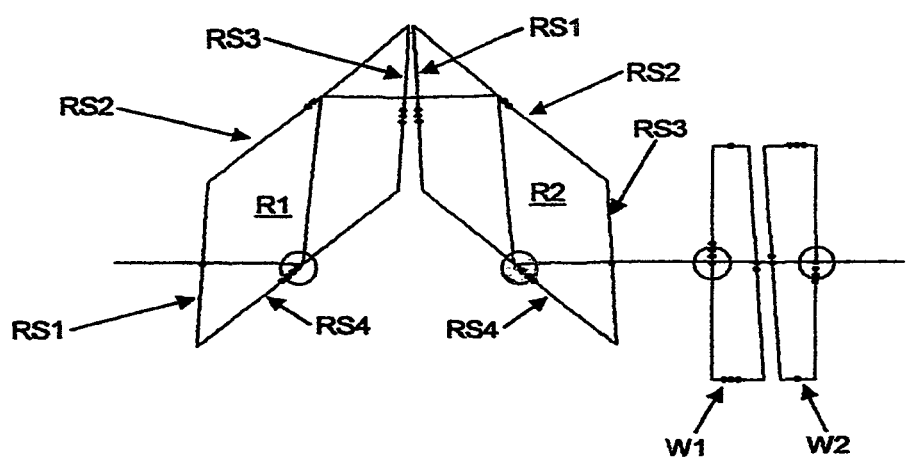
FIG. 4d shows how two Fresnel Rhombs, each of which is equivalent to two right angle prisms in FIG. 4c, and two wedges, can be combined to result in an angularly non-deviated beam.

FIG. 4c shows a variation on FIG. 4b which is believed new and novel even without surface coatings. Shown are four similar right angle prisms, (ie. first (ra), second (rb), third (rc) and forth (rd)), having sides opposite their right angles of, respectively, (ha) (hb) (hc) and (hd). As viewed in FIG. 4c the first right angle prism (ra) is positioned so that its side (ha) opposite the right angle thereof is facing downward and to the right. Directly above the first right angle prism (ra) is the second right angle prism (rb), which is oriented so that its side (hb) opposite the right angle thereof is facing upward and to the left. Directly to the right of the second right angle prism (rb) is the third right of right angle prism (rc) which is oriented so that its side (hc) opposite the right angle thereof is facing upward and to the right. Finally, positioned directly below the third right angle prism (rc) is the forth right angle prism (rd), oriented so that its side (hd) opposite the right angle thereof is facing downward and to the left. Note that the sides of each element (ra) (rb) (rc) and (rd) adjacent to the right angles thereof are identifiable as "right angle sides". It is also noted that the sides of elements (ra) (rb) (rc) and (rd) opposite the right angles can be coated with a material of different refractive index material, (eg. where said elements are made of fused silica the coating can be, for instance, 35 nm of lower index $MgF_2$). Such a coating makes the retardence entered by a total internal reflection from a side opposite the right angle thereof substantially achromatic with range of retardation. Also shown in FIG. 4c are two optional Wedge Elements (w1) and (w2), the purpose of which is described with respect to FIG. 12b. It is also noted that the design of FIG. 4b is believed to be new and novel when a coating is applied to a reflective outer surface thereof. FIG. 4d shows how two Fresnel Rhombs (R1) (R2) which are equivalent to the four right angle prisms (ra)+(rb) and (rc)+(rd) of FIG. 4c, and two wedges (w1) (w2), can be combined to result in an angularly non-deviation of a beam (B) caused to pass therethrough. The angles of the Rhombs are 45, 135, 45 and 135 degrees. Coatings with a different refractive index from that of the material from which the Rhomb is comprised can be present on surfaces thereof as well, much as for the system in FIG. 4b.

It is noted that when applying the embodiments of FIGS. 4b and 4d, the Beam (B) is typically not entered exactly along a normal to the surface entered, (eg. (RS1) in FIG. 4d). This diverts unwanted depolarizing secondary bounces out of the primary beam and such a beam entry locus can be termed "substantially normal" to the surface where the off-normal angle is sufficient to divert said reflections. A typical off-normal angle is about three (3) degrees which angularly deviates transmitted secondary beams by about six (6) degrees. This is sufficient to provide separation from the primary transmitted beam. Also, as presented with respect to FIG. 12b, the Wedges (w1) (w2) can be rotated with respect to one another and/or simultaneously to result in an angularly non-deviated beam, (B).

Figure 4E:
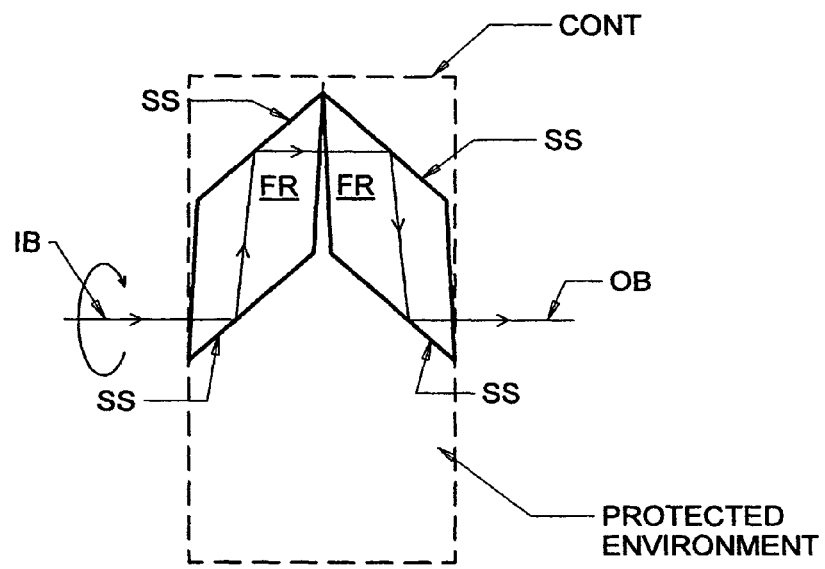
FIGS. 4e-4i show a containing system for mounting FIG. 4b Fresnel Rhombs.
Figure 4F:
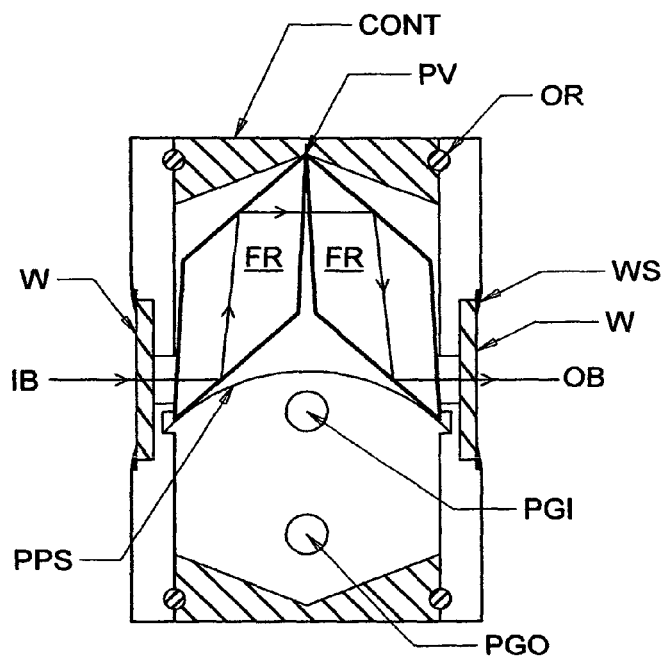
Figure 4G:
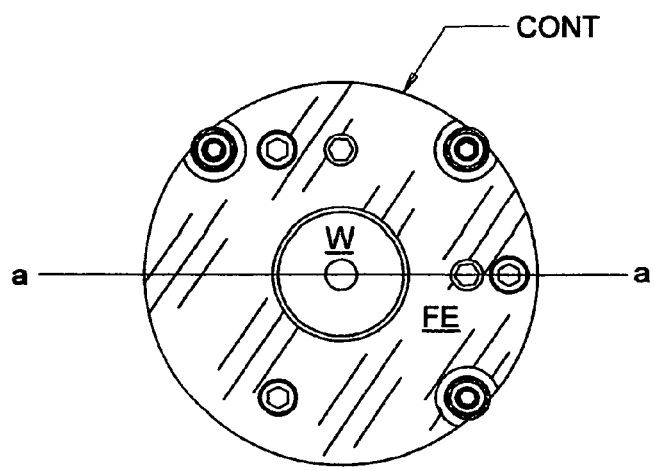

FIGS. 4e-4g show a Front Elevational view of the outside of a Containing System (CONT) for mounting FIG. 4b systems, or slight variations thereof, (eg. two FIG. 4a Fresnel Rhombs), and this comprises a focus of the present invention as presently Claimed. Note FIGS. 4e and 4f show two FIG. 4a Fresnel Rhombs (FR) system mounted in said Containing System (CONT), such that the two Fresnel Rhombs (FR) are oriented with respect to one another as desired. Typically, to divert away reflections, it is desired to have side (RS3), (see FIG. 4b), of the first Fresnel Rhomb slightly offset from parallel to side (RS1), (again see FIG. 4b), of the second, and the present Containment System (CONT) provides a convenient approach to achieving this result. FIG. 4f shows greater detail of the Containment System (CONT) including indication Windows (W) through which a beam of electromagnetic radiation enter and, after passing through said system of Fresnel Rhombs, exit. Also indicated are means for Entering Purge Gas (PGI), and exiting Exiting Purge Gas (PGO). In use it is important that contaminants not accumulate of sides (SS) of the Fresnel Rhombs. In use, when constructing the combination Containment System (CONT) and contained system of Fresnel Rhombs (FR), a purging gas is caused to flow through the inner volume of the Containment System (CONT) after the Fresnel Rhombs (FR) are mounted therein and the Containment System (CONT) is sealed. This is essential as the slightest amount of contaminant on the Sensitive Sides (SS) of the Fresnel Rhombs (FR) can cause undesired change in the phase delay entered to a polarized beam by an internal reflection thereof from a contaminated outer surface (SS). FIG. 4f also shows a Spring (PPS) which serves to secure the two Fresnel Rhombs (FR) in the Containment (CONT) in a manner which does not cause stress therein. This is an important aspect of the Container (CONT) design, as stress applied to a Fresnel Rhomb (FR) can change the optical characteristics thereof.

Figures 4H, 4I:
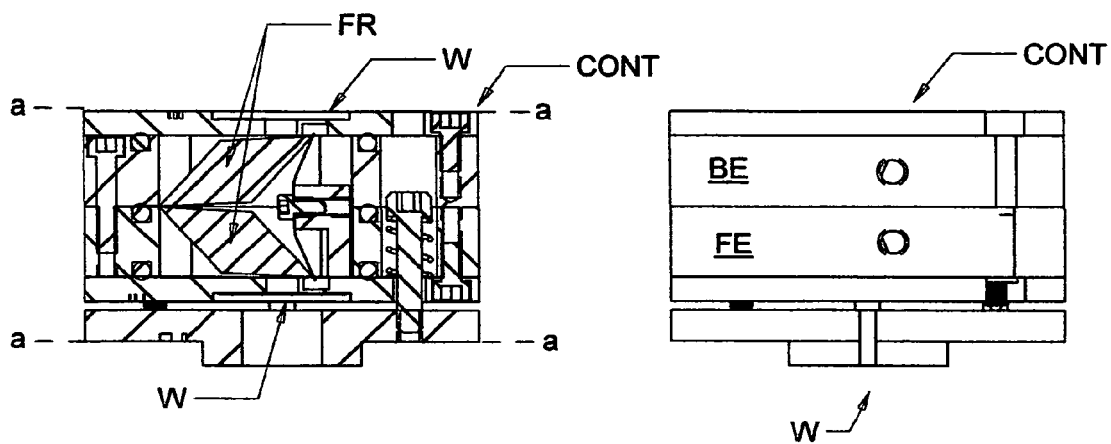

FIG. 4g shows more detail, in front elevation, of preferred embodiment of the system shown in FIGS. 4e and 4f, and FIG. 4h serves to indicate the Containment System (CONT) presents a barrier between an outer environment and the inner volume thereof. FIG. 4i shows, in side elevation, that the Containment System (CONT) appears substantially rectangular, with a line projecting longitudinally, centrally. The line is the result of a Back Element (BE) coming into contact with the FIG. 4e Front Element (FE), which, but for provision for the presence of means for Entering Purge Gas (PGI) and exiting Exiting Purge Gas (PGO), and the Window (W) construction, appears similar to the front element.

In more detail, the Containment (CONT) for Fresnel Rhombs (FR), (ie. prisms), comprises abutting front (FE) and back (BE) elements which, as viewed in frontal elevation are circular in shape, and which, as viewed in side elevation, is substantially rectangular in shape. In cross-section the Containment (CONT) internally comprises two sides projecting from a "peak" (PV) location whereat, in use, the point of intersection of sides two (RS2) and three (RS3) of one Fresnel Rhomb, and the point of intersection of sides one (RS1) and two (RS2) (see FIG. 4b) of a second Fresnel Rhomb (FR) make contact in a manner resulting in side three (RS3) of one and side one (RS1) of the other are oriented slightly off-parallel with respect to one another. Said containment further comprises recessed regions into which ends of a spring element (PPS) insert so as to cause it to be bowed toward said peak location, in a manner enabling said spring to contact the fourth (RS4) sides of both Fresnel Rhombs. The result is that two Fresnel Rhombs (FR) entered into the Containment (CONT) are fixed in position therewithin in an intended orientation with respect to one another without there being stress causing forces applied thereto. The above described system further causes side one (RS1) of one Fresnel Rhomb, and side three (RS3) of the other Freshenl Rhomb to be oriented with respect to the Windows (W) in the Front (FE) and Back (BE) elements of the Containment (CONT) system such that an Input beam (IB) of electromagnetic radiation and an Output beam (OB) thereof enter one (RS1) (RS3) side and exit the other (RS3) (RS1), respectively. In use, total internal reflections inside the Fresnel Rhombs enter specific amounts of retardation into the polarization state of the Input beam (IB), which exists as Output beam (OB).

Figure 3C:
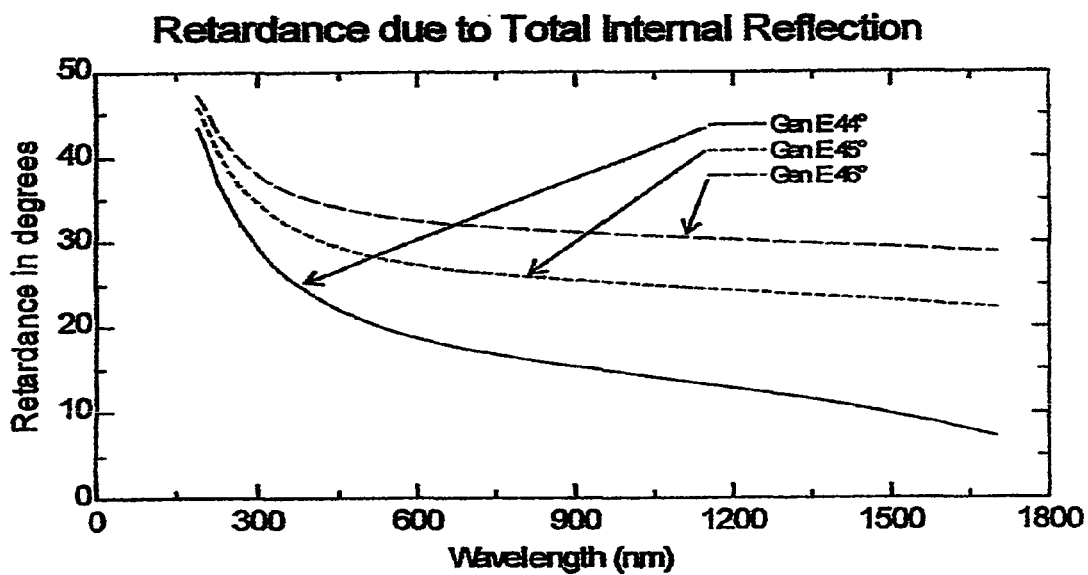
FIG. 3c shows retardence vs. and wavelength, (at a given angle), for the fused silica/air interface for a system as shown in FIG. 4c.
Figure 3A:
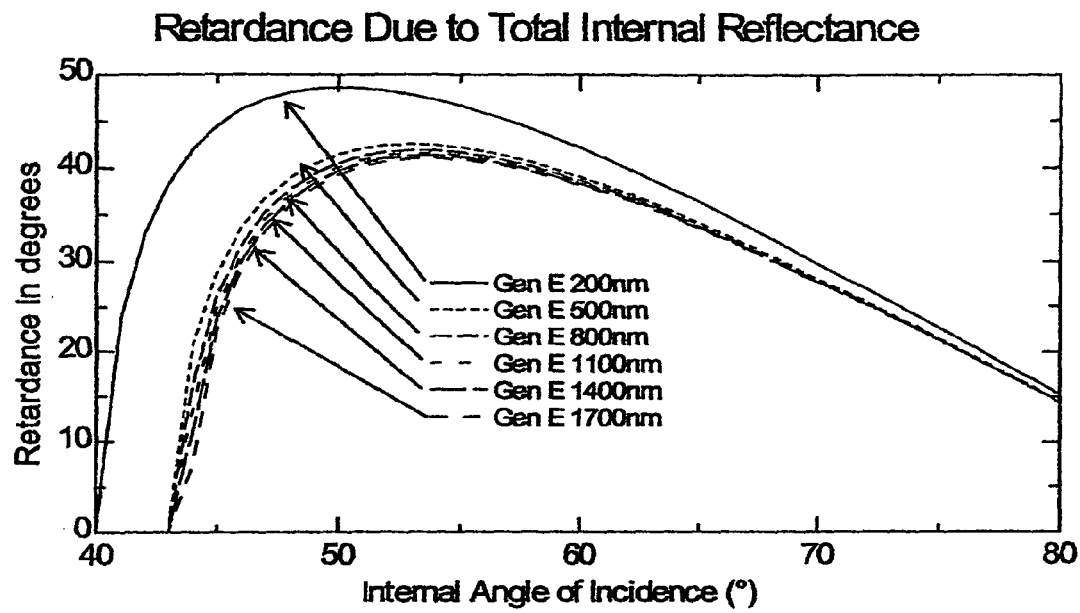
FIGS. 3a and 3b show retardence vs. internal angle and wavelength, (at a given angle), for the fused silica/air interface.
Figure 3B:
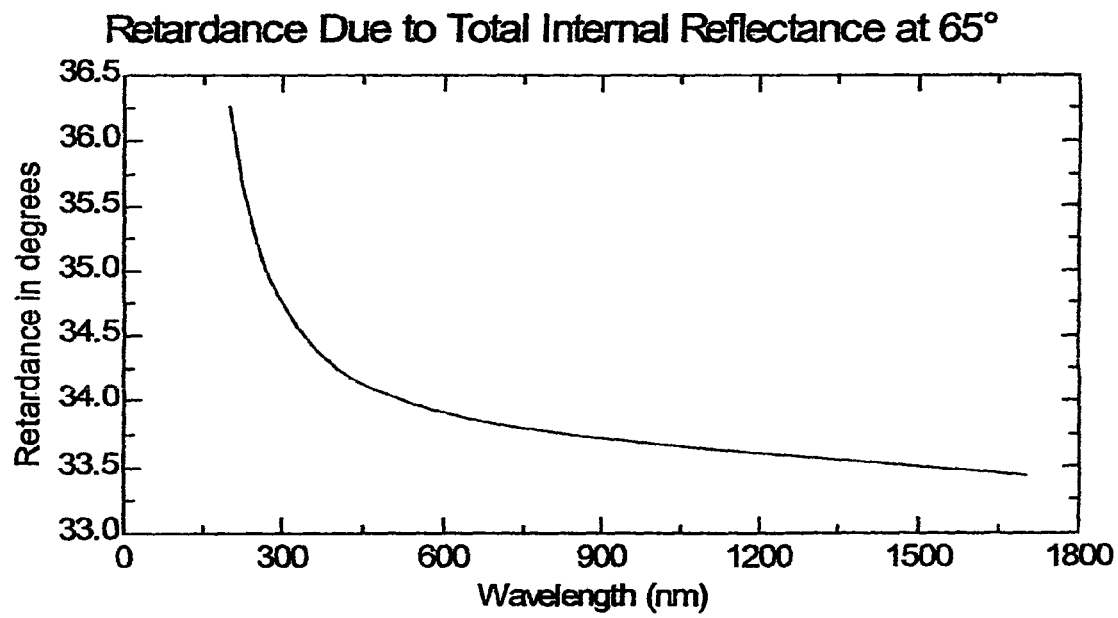
Figure 3D:
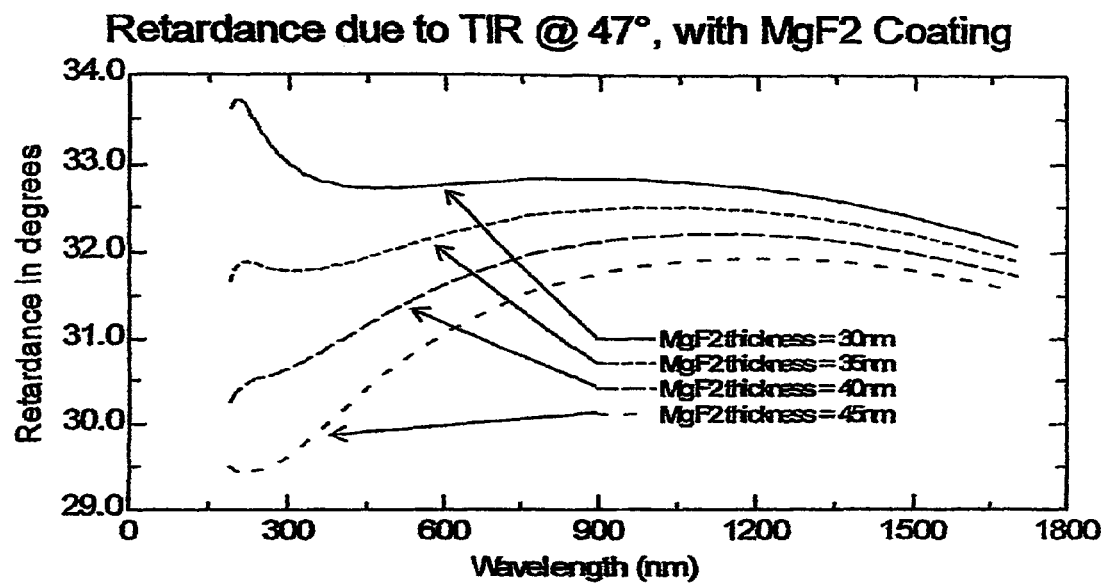
FIG. 3d show results as in FIG. 3c, but for a system having a different refractive index coating on reflective surfaces of a system as shown in FIG. 4c.

FIG. 3c shows retardence vs. total internal reflection angle and wavelength, (at a given angle), for the fused silica/air interface for a system as shown in FIG. 4c, and FIG. 3d show results as in FIG. 3c, but for a system having a different refractive index coating on reflective surfaces of a system as shown in FIG. 4c. FIGS. 3a and 3c indicate that near a 45 degree angle of incidence the retardence varies strongly as a function of both wavelength and angle of incidence. A total retardence, resulting from four reflections, varies between 180 degrees at 190 nm to less than 90 degrees at 1700 nm. FIG. 3d indicates that including a coating on the side of the elements (ra) (rb) (rc) and (rd) opposite their right angle can make said result more achromatic. For instance, where the elements (ra) (rb) (rc) and (rd) are made from Fused Silica, and the coatings are between 20-90 nm of $MgF_2$, the total retardation for four total internal reflections in the described system is between 116 and 136 degrees over a range of wavelengths of 190 nm-1700 nm.

Figure 5:
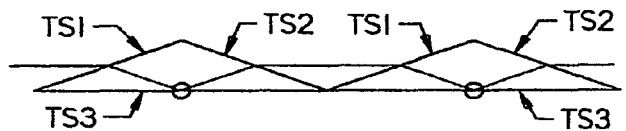
FIG. 5 shows two triangular isosceles prisms, with angles of 26, 128, and 26 degrees.

Continuing, the present invention retarder design uses an even number of multiple total internal reflections to provide the desired amount of retardation. Furthermore, the geometry of the reflections is such that a given change in the input beam angle causes opposite changes in the internal angles of reflection, and therefore. (since the slope of the retardance vs. total internal reflection angle curve, (see FIG. 3a), above is relatively linear over small angle ranges), the net retardation of the system does not change to the 1st order for small changes in the angle of beam entrance. One embodiment of the new retarder system is shown in FIG. 5. Shown are two triangular isosceles prisms, each with angles of 26, 128, and 26 degrees. Each triangular shaped prisms each has:

first (TS1) and second (TS2) sides of equal length which project from one another at an angle greater than ninety degrees therebetween, and a third side (TS3) oriented opposite said greater than ninety degree angle, said at least two similar triangular shaped prisms being oriented with respect to one another such that the third (TS3) sides thereof are substantially colinear;

such that a beam of electromagnetic radiation caused to enter the first side of the first thereof, at a non-normal angle thereto, is refracted so that it internally reflects from said third side thereof, then exits said second side thereof in a direction such that it then enters the first side of another thereof at a non-normal angle thereto, is refracted so that it internally reflects from said third side thereof, then exits said second side thereof. The prisms can be fabricated from fused silica.

Figure 6:
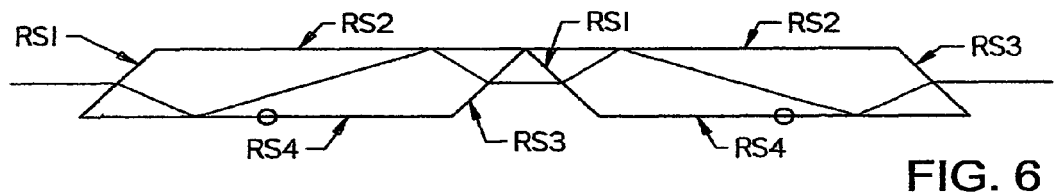
FIG. 6 shows two parallelogram rhombs, with angles of 36, 144, 36, and 144 degrees.
Figure 7A:
FIGS. 7a, 7b, 8a and 8b show that if the elements are translated up or down, the exiting beam is unchanged.
Figure 7B:
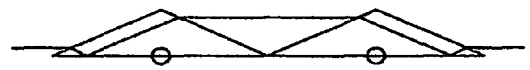
Figure 8A:
Figure 8B:

Another embodiment of the new retarder system is shown in FIG. 6. Shown are two parallelogram rhombs, with angles of 36, 144, 36, and 144 degrees. Said parallelogram shaped rhombs, each have first (RS1), second (RS2), third (RS3) and forth (RS4) sides, said first (RS1) and third (RS3) sides being substantially parallel to one another and said second (RS2) and forth (RS4) sides being substantially parallel to one another, said first (RS1) and second (RS2), and said third (RS3) and forth (RS4) sides of the first parallelogram shaped rhomb meeting one another at angles greater than ninety degrees therebetween, and said second (RS2) and third (RS3) sides and said first (RS1) and forth (RS4) sides thereof meeting one another at angles less than ninety degrees therebetween. Said at least two parallelogram shaped rhombs are oriented with their second (RS2) sides being substantially colinear and with their forth (RS4) sides thereof being substantially colinear, such that a beam of electromagnetic radiation caused to enter the first side (RS1) of the first parallelogram shaped rhomb, at a non-normal angle thereto, is refracted so that it internally reflects from said forth (RS4) and second (RS2) sides thereof, then exits said third (RS3) side thereof in a direction such that it then enters the first (RS1) side of the second thereof at a non-normal angle thereto, is refracted so that it internally reflects from said second (RS2) and forth (RS4) side thereof, then exits said third (RS3) side thereof. The parallelogram shaped rhomb can be fabricated from fused silica.

Note that both the FIG. 5 and FIG. 6 embodiments have input and output surfaces into which a beam is entered, and out of which is exits, respectively, said surfaces serving to refract the beam in use. Other surfaces at which total internal reflection occurs are used to enter retardence. It is noted that the Fresnel losses at the refracting interfaces result in a relative attenuation for orthogonally polarized beams. The orthogonal beams are typically denoted p and s for light polarized parallel and perpendicular to the plane of incidence. The relative attenuation and retardation of an optical element can be quantified by the equation below, which is similar to the standard ellipsometry definition. In this case, Tp and Ts are the complex amplitudes of the orthogonal beams which are transmitted through the prism, ($\psi$) is the relative attenuation, and ($\Delta$) is the retardence:

$$Tp/Ts = \tan(\psi)e^{i(\Delta)}.$$

An ideal retarder changes only the relative p-to-s phase, (ie. the retardation), of the beam, and for said case ($\psi$)=45 degrees. For the current invention, the ($\Delta$) value depends on the number and angle of refracting surfaces in the design. For the triangle design ($\psi$) is about 57 degrees, and for the rhomb design ($\psi$) is about 53 degrees. Since ($\psi$) is dependent on the index of refraction, it varies a few degrees over the 190-1700 nm spectral range). While the ($\psi$) value of the retarder does have to be determined in the ellipsometer/polarimeter system calibration, the sensitivity and accuracy of the instrument has been found to not be significantly degraded as long as ($\psi$) is not too far from 45 degrees. It is noted that the beam enters and exits the elements at near a Brewster angle of incidence, hence substantially 100% of the p polarized light is transmitted through the system.

The geometry and symmetry of the elements results in a number of very useful properties. For example, FIGS. 7a, 7b, 8a and 8b show that if the sequential elements are translated up or down as a unit, the exiting beam remains collinear with the input beam. If the sequential elements are rotated, FIGS. 9a, 9b, 10a and 10b show that the exiting beam angle is unchanged, (though it is slightly translated).

FIGS. 11a, 11b, 11c, 11d, 11e, 11f show that the most useful property of the new retarder design is that as the angle of the input beam is changed, the resulting polarization properties ($\psi$) and ($\Delta$) change very little. This is because the geometry and symmetry of the designs are such that changes in the refraction and total internal reflection angles have opposite signs for the two elements shown in the system of FIGS. 7a, 7b, 8a and 8b, which in turn cancels change in (ψ) and (Δ) vs. input beam angle to a 1st order approximation. To give a feel for the results achieved by a present invention system, typically the change in (ψ) and (Δ) for a one degree change in beam angle is approximately 0.01 degree. Note that FIGS. 11a-11f show that:

Beam angle=+1 degrees, (ψ)=56.953, (Δ)=70.425;
Beam angle=0 degrees, (ψ)=56.940, (ψ)=70.419;
Beam angle=−1 degrees, (ψ)=56.953, (Δ)=70.425;
Beam angle=+1 degrees, (ψ)=52.357, (Δ)=114.232;
Beam angle=0 degrees, (ψ)=52.349, (Δ)=114.221;
Beam angle=−1 degrees, (ψ)=52.357, (Δ)=114.232.

The net relative attenuation and retardance ( ) and ( ) of the system can be controlled by adjusting the number of total internal reflections (determined by the number and length of the elements), the angles of refraction and reflection (determined by the prism and/or rhomb angles), and the material used to fabricate the elements.

Any transparent, optically isotropic material can be used for the elements, though care should be taken in mounting the elements to minimize strain-induced birefringence. Fused silica is ideal for the UV-VIS-NIR spectral range, but CaF2 is preferable in the DUV, and Si, Ge, ZnSe, KRS5, etc. are suited for use in the IR. Presently, preferred embodiment designs use fused silica, and have the following properties over a wide 190-1700 nm spectral range:

triangular prisms: (ψ)=56.382-59.286; (Δ)=67.801-81.290;
parallelogram rhombs:
(ψ)=51.976-54.271; (Δ)=109.795-135.701.

Said examples are not to be considered limiting, however, and other designs are possible, using different materials, angles, and/or geometries. For instance, it might be beneficial to provide for substantially normal angle entry and exit thereby avoiding the effect on (ψ), but the key element of any design is that symmetry is employed to enable the following properties:

1. The locus of the beam is not angularly deviated as the system is translated;
2. The angle of the beam locus is not angularly deviated as the system is rotated;
3. The change in polarization properties are minimal for changes in the input beam angle.

Another beneficial aspect of the disclosed design is that, since at least two elements are present, if the elements are not perfectly fabricated and/or aligned, the height and/or tilt of at least one of the elements can be adjusted with respect to the other such that the input beam is substantially angularly undeviated in position and angle by the system. FIG. 12a demonstrates a system for accomplishing this by allowing translation and/or rotation of an element, and FIG. 12b shows an additional sequential two wedge (w1) (w2) system wherein relative rotation of one wedge with respect to the other provides a similar benefit. A system can then include at least one selection from the group consisting of:

at least one of the sequential elements has a mechanism for translating and/or tilting the element, for the purposes of aligning the system such that the output beam is substantially angularly undeviated from said input beam;
there is present an additional sequential two wedge system wherein relative rotation of one wedge with respect to the other and/or combined wedge rotation can be performed for the purposes of aligning the system such that the output beam is substantially angularly undeviated from said input beam.

It is also noted that when practicing Beam (B) angular deviation correction via Wedge (w1) (w2) rotations, relative rotation of one wedge with respect to the other and combined rotations of both Wedges (w1) and (w2) can be practiced.

It is noted that while not shown or preferred, a system could comprise such as one Triangular shaped element and one Trapezoidal shaped element. Such an arrangement can be viewed as a sequence of a FIG. 9a and FIG. 10a embodiment, perhaps with one of the FIG. 9a prisms removed and with one of the FIG. 10a rhombs removed. Careful attention to preserving effective symmetry is required in any such embodiment, however.

It is also noted that only a single primary beam is transmitted through the disclosed systems, as the secondary reflections from the refracting interfaces do not re-enter the primary beam path. This means that only a single polarization state is present in the transmitted beam. In contrast, multiple reflections from the parallel surfaces of birefringent plate retarders result in beam depolarization which can degrade the ellipsometer/polarimeter accuracy if not properly taken into account.

Figure 13:
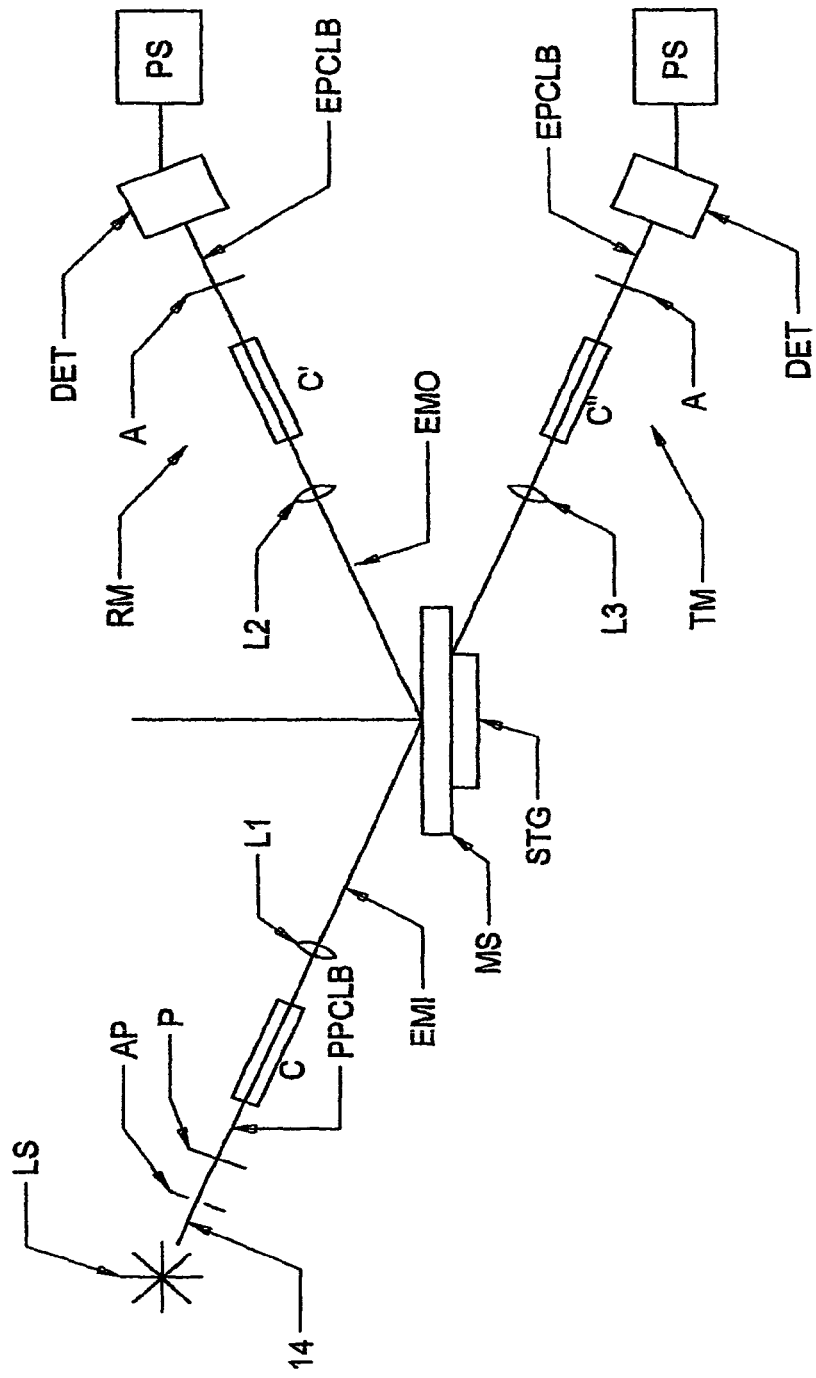
FIG. 13 shows a basic ellipsometer or polarimeter comprising at least one rotatable compensator system.

As a primary use of the sequential element system is in ellipsometer and polarimeter systems, FIG. 13 is included to show an ellipsometer or polarimeter system which, for each of a Reflection and Transmission mode, comprises:

a) a source (LS) of electromagnetic radiation;
b) a polarizer (P);
c) a stage (STG) for supporting a sample (MS);
d) an analyzer (A); and
e) a detector (DET);

said ellipsometer or polarimeter system further comprises at least one rotatable compensator (C) (C') (C") present at least one location selected from the group consisting of:

between said source (LS) of electromagnetic radiation and said stage (STG) for supporting a sample (MS); and
between said stage (STG) for supporting a sample (MS) and said detector (DET);

said at least one rotatable compensator (C) (C') (C") comprising at least two sequential elements oriented with respect to one another such that said entered electromagnetic beam undergoes total internal reflection at least once in each of the elements, with the orientation, geometry, and symmetry of the elements being such that the output beam position is angularly undeviated by a translation of the system, and the output beam angle is angularly undeviated by a rotation of the system about the beam locus. Again, one embodiment provides that two triangular shaped prisms are used for the elements. Preferred design provides that the angles of the triangular prisms are 26, 128, and 26 degrees, and fabrication of the prisms can be from fused silica. Another embodiment provides that two parallelogram shaped rhombs are used for the elements. Preferred design provides that angles of the parallelogram shaped rhombs are 36, 144, 36, and 144 degrees, and again, fabrication of the parallelogram can be from fused silica. Also, as mentioned other embodiments can include one or more triangular shaped prisms and one or more parallelogram shape rhombs etc. Further, at least one of the elements can have a mechanism for translating and/or tilting at least one of the elements, for the purposes of aligning the system such that the locus of the exiting beam is substantially angularly undeviated in position and angle from the locus of the input beam.

Figure 14:
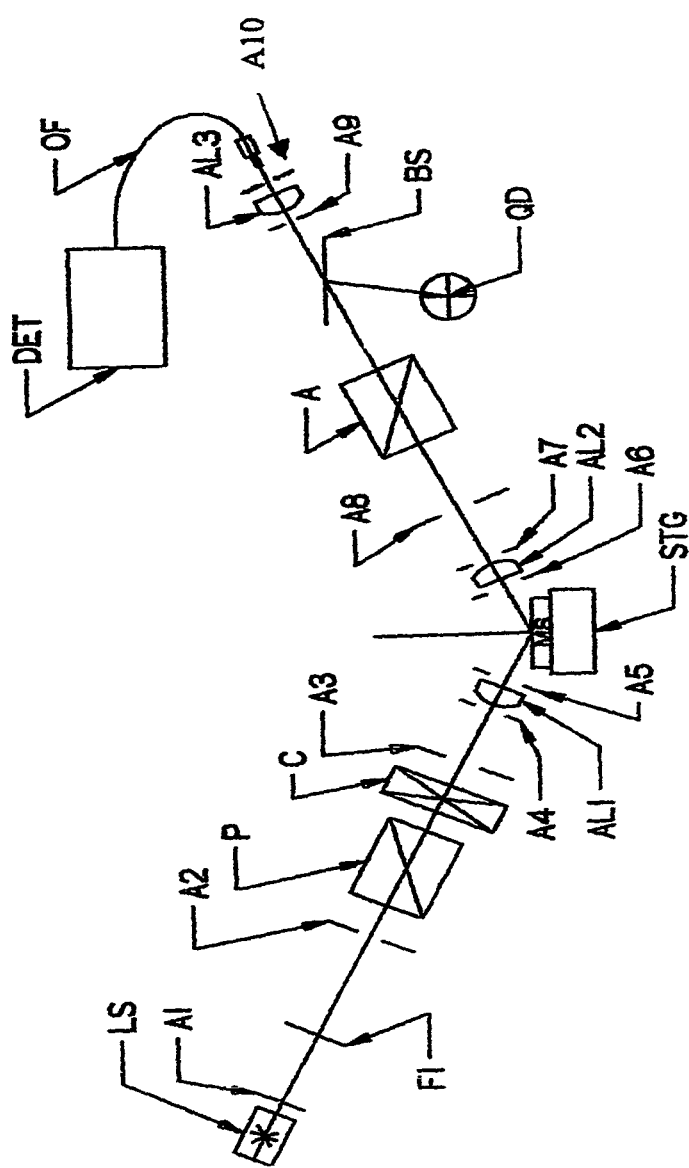
FIG. 14 shows a spectroscopic rotating compensator material system investigation system.

FIG. 14 shows that a present invention ellipsometer or polarimeter system, comprising a source (LS) of polychromatic beam of electromagnetic radiation, a first aperture (A1), a second aperture (A2), a fixed polarizer (P), a rotating compensator (C), a third aperture (A3), a forth aperture (A4), a first substantially achromatic lens (AL1), a fifth aperture (A5), a stage (STG) for supporting a material system, a sixth aperture (A6), a second substantially achromatic lens (AL2), a seventh aperture (A7), an eighth aperture (A8), a fixed analyzer (A), a ninth aperture (A9), a third substantially achromatic lens (AL3), an optical fiber (OF) and a detector system (DET) which contains a dispersive element and a multiplicity of detector elements, there further being a UV filter (F1) present between said source (LS) of polychromatic beam of electromagnetic radiation and said stage (STG) for supporting a material system. When said spectroscopic rotating compensator material system investigation system is used to investigate a material system (MS) present on said stage (STG) for supporting a material system, said fixed analyzer (A) and fixed polarizer (P) are maintained essentially fixed in position and said rotating Compensator (C) is caused to continuously rotate while a polychromatic beam of electromagnetic radiation produced by said source (LS) of a polychromatic beam of electromagnetic radiation is sequentially caused to pass through said first aperture (A1), second aperture (A2), fixed polarizer (P), rotating compensator (C), third aperture (A3), forth aperture (A4), first substantially achromatic lens (AL1), fifth aperture (A5), said polychromatic beam of electromagnetic radiation also passing through said UV filter, then interact with a material system (MS) placed on said stage (STG) for supporting a material system (MS), then sequentially pass through said sixth (A6) aperture, second substantially achromatic lens (AL2), seventh aperture (A7), eighth aperture (A8), fixed analyzer (A), ninth aperture (A9), third substantially achromatic lens (AL3), optionally pass through a beam shaping aperture (A10), and then enter said optical fiber (OF) and therevia enter said detector system (DET).

Figure 15:
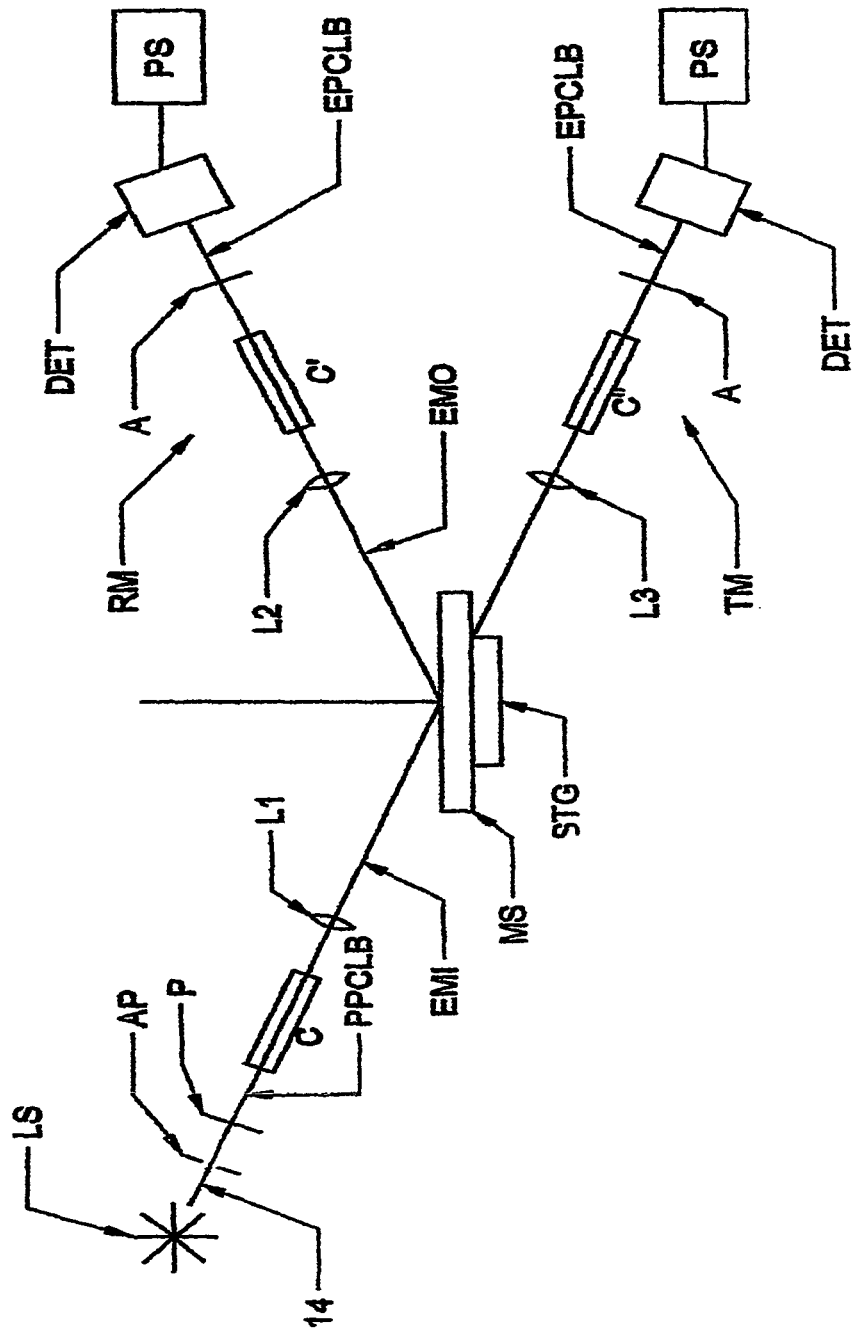
FIG. 15 shows that a present invention ellipsometer or polarimeter system.

FIG. 15 shows that a present invention ellipsometer or polarimeter system, for each of a Reflection and Transmission mode, can comprise:
 a) a source (LS) of electromagnetic radiation;
 b) a polarizer (P);
 c) a stage (STG) for supporting a sample (MS);
 d) an analyzer (A); and
 e) a detector (DET);
said ellipsometer or polarimeter system further comprises at least one rotatable compensator (C) (C') (C") present at least one location selected from the group consisting of:
 between said source (LS) of electromagnetic radiation and said stage (STG) for supporting a sample (MS); and
 between said stage (STG) for supporting a sample (MS) and said detector (DET);
said at least one rotatable compensator (C) (C') (C") comprising at least two sequential elements oriented with respect to one another such that said entered electromagnetic beam undergoes total internal reflection at least once in each of the elements, with the orientation, geometry, and symmetry of the elements being such that the output beam position is angularly undeviated by a translation of the system, and the output beam angle is undeviated by a rotation of the system about the beam locus. Again, one embodiment provides that two triangular shaped prisms are used for the elements. Preferred design provides that the angles of the triangular prisms are 26, 128, and 26 degrees, and fabrication of the prisms can be from fused silica. Another embodiment provides that two parallelogram shaped rhombs are used for the elements. Preferred design provides that angles of the parallelogram shaped rhombs are 36, 144, 36, and 144 degrees, and again, fabrication of the parallelogram can be from fused silica. Also, as mentioned other embodiments can include one or more triangular shaped prisms and one or more parallelogram shape rhombs etc. Further, at least one of the elements can have a mechanism for translating and/or tilting at least one of the elements, for the purposes of aligning the system such that the locus of the exiting beam is substantially angularly undeviated in position and angle from the locus of the input beam.

It is also mentioned that in the following it will be generally assumed that a Material System (MS) under investigation by a Spectroscopic Rotating Compensator Material System Investigation System is positioned upon the Material System Supporting Stage (STG). This need not be the case, as is described in U.S. Pat. No. 5,706,087 wherein a Material System (Sample), (MS) can be positioned in a Magneto-Optic System which is physically too large to be supported by said Material System Supporting Stage (STG), or in an environmental control chamber. Further, especially where Ultraviolet range wavelengths are utilized, the system of FIG. 13, 14 or 15 can be placed into an evacuated or purged, (eg. by nitrogen or argon), Chamber to the end that UV absorbing Oxygen and Water Vapor are not present therewithin. The entire FIG. 13, 14 or 15 system can be so encompassed within a said Chamber, or only the Sample (MS) Stage portion thereof. The Chamber can be of multiple region construction and can be interpreted to contain one or multiple interior regions. For instance the FIG. 1a Pre-(MS) Polarization State Generator (PSG) and Post-(MS) Polarization State Detector (PSD) can be open to a region containing the Material System (MS), or can be considered to be sequestered by (AC1) and (AC2) so that the internal environments available to each can be controlled to be are the same or different. More specifically, the environmental chamber can have a configuration characterized by a selection from the group consisting of:
 it comprises at least one chamber region in which is present polarization state generator (PSG) comprising component(s) prior to said material system, said material system (MS), and polarization state detector (PSD) comprising component(s) after said material system;
 it comprises at least three chamber regions, in one of which is present polarization state generator (PSG) comprising component(s) prior to said material system (MS), in the second of which is present the material system (MS) and in the third of which is present polarization state detector (PSD) comprising component(s) after said material system (MS);
 it comprises at least two chamber regions, in one of which is present polarization state generator (PSG) comprising component(s) prior to said material system (MS) and said material system (MS), and in the second of which is present polarization state detector (PSD) comprising component(s) after said material system MS;
 it comprises at least two chamber regions, in one of which is present polarization state generator comprising component(s) prior to said material system, and in the second of which is present polarization state detector comprising component(s) after said material system and said material system.

The environment in any chamber region can be individually controlled, or the environment in all chamber regions can be similarly controlled. This includes allowing the chamber regions containing the polarization state generator (PSG) and the polarization state detector (PSD) to be in ambient with only a material system (MS) under investigation being in a Controlled Environment (SES). The functional purpose is to avoid attenuation of wavelengths (eg. UV) by the presence of oxygen or water vapor etc.

It is noted that the coating of, for instance, a material of different refractive index material, (eg. where said elements are made of fused silica the coating can be, for instance, 35 nm of $MgF_2$, which has a lower index), applied to a totally internally reflecting surface described with respect to FIGS.

4b and 4c can be applied in any of the embodiments in FIGS. 5, 6 7a, 7b, 8a, 8b, 9a, 9b, 10a, 10b, 11a-11f and 12a and 12b. Further, such a coating can be beneficially placed on non-totally internally reflecting surfaces thereof to reduce reflections therefrom It is noted that as regards, for instance, FIGS. 4b, 4d and 6, the rhombs, (eg. (R1) and (R2) in FIG. 4d), are oriented as functional mirror images of each other, while the side the input beam enters is, in both instances, labeled (RS1). It is felt this was the best way to disclose the invention, however, it might lead to some confusion regarding angles between, say, sides (RS1) and (RS2). In the foregoing discussion that angle is identified as being greater than 90 degrees. This is valid for the first (RS1) shown rhomb. For purposes of understanding the foregoing discussion, however, in mirror image the sides (RS1) and (RS3) in the second rhomb (RS2) can be considered reversed when the angles therebetween are described as are those in the first rhomb (RS1).

Finally, to avoid confusion, the terminology "beam locus" can be read "beam path", and the terminology "similar elements" should be read to mean that the elements were produced with an intent that they be identical. However, even with that intent in practice elements are not usually identical as regards, for instance, beam angular deviation caused thereby when an electromagnetic beam is passed therethrough.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. An ellipsometer or polarimeter system comprising:
   a) a source of electromagnetic radiation;
   b) a polarizer;
   c) a stage for supporting a sample;
   d) an analyzer; and
   e) a detector;
   said ellipsometer or polarimeter system further comprising at least two rotating or rotatable compensator systems present at at least one location selected from the group consisting of:
      both between said source of electromagnetic radiation and said stage for supporting a sample;
      both between said stage for supporting a sample and said detector; and
      one thereof being between said source of electromagnetic radiation and said stage for supporting a sample, and the other thereof being between said stage for supporting a sample and said detector;
   said at least two rotating or rotatable compensators each comprising at least two sequential compensator elements oriented with respect to one another such that said entered electromagnetic beam undergoes internal reflection at least once in each of the elements, with the sequence, orientation, geometry, and symmetry of the elements being such that the locus of the output beam is substantially angularly undeviated from that of the input beam by a translation of the system, and the locus of the output beam angle is substantially angularly undeviated from that of the input beam by a rotation of the system about said beam locus;
   said ellipsometer or polarimeter system further comprising means for causing said each rotating or rotatable compensator to rotate at a desired rotation rate, which rate for one said compensator is the same as, or different than that of another thereof; and
   said ellipsometer or polarimeter system further comprising, for each compensator system, a containment system with provision for receiving selected compensator elements thereinto and orienting them in a desired relationship with respect to one another, and in which said selected elements are present.

2. An ellipsometer or polarimeter system as in claim 1, wherein said at least one rotating or rotatable compensator comprises two sequential parallelogram shaped rhombs as compensator elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween,
   said two parallelogram shaped rhombs being oriented with their first and third sides being substantially parallel to one another, wherein "substantially parallel to one another", means that said third (RS3) side of said first and first (RS1) side of the second of said parallelogram shaped rhombs are offset from being parallel to one another by no more than about +/−ten (10) degrees;
   such that a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof.

3. An ellipsometer or polarimeter system as in claim 2, in which at least one of the first RS1, second RS2, third RS3 and forth RS4 sides of at least one of the compensator elements is coated with a material having a different refractive index than of the retarder.

4. An ellipsometer or polarimeter system as in claim 2, in which two of said at at least two compensators are fabricated from fused silica, and at least sides RS2 and RS4 of both compensators are coated with $MgF_2$.

5. An ellipsometer or polarimeter system as in claim 1, in which said containment system is characterized by:
   an outer enclosure which separates an outer environment from the enclosed inner volume in which is present said provision for receiving selected elements thereinto in a desired relationship with respect to one another therewithin; in which the containment system is further characterized in that said outer enclosure further comprises means for flowing purging gas into and out of said enclosed inner volume such that the inner volume is caused to contain a gas which is not damaging to outer surfaces of said selected elements caused to be present therein;
   such that in use a gas is caused to flow into said enclosed inner volume through said means for flowing purging gas into said enclosed inner volume, such that some amount thereof passes through said inner volume and out of said means for flowing gas out of said inner volume; and optionally, following a sufficient purging, sealing said means for flowing purging gas into and out of said enclosed inner volume such that outside environment can not thereafter enter into said inner volume; to the end that the inner volume is caused to contain said gas in contact with the outer surfaces of said selected elements caused to be present therein.

6. A method of constructing a multiple element compensator system for introducing a relative phase retardation between orthogonal components of a polarized beam of electromagnetic radiation entered thereinto, said multiple element compensator system comprising at least two similar elements which are sequentially secured with respect to one another such that a beam of electromagnetic radiation entered to the first thereof undergoes internal reflection at least once in each of the at least two elements, and exits the second thereof along a locus which is not angularly deviated or laterally offset from that of said entered beam by more than acceptable amounts; said method comprising, before practice of step d, the steps of:
  a) providing a multiplicity of similar elements;
  b) experimentally determining and recording data describing measured angular deviation entered to a beam of electromagnetic radiation by interaction with each of said multiplicity of similar elements individually;
  c) defining acceptable beam angular deviation and laterally offset values and providing a computer program which is capable of analyzing said data recorded in step b;
said method further comprising the steps of:
  d) applying said computer program provided in step c to data recorded in step b the end that pairings of similar elements are identified which in sequence meet the acceptable beam angular deviation values identified in step c;
  e) selecting at least one of said pairings of similar elements identified in step d and securing the paired similar elements in a sequential system, then experimentally monitoring angular deviation entered to a beam of electromagnetic radiation entered to a first thereof, so that it undergoes internal reflection at least once in each of the at least two elements, and then exits the second thereof;
  f) determining if the beam angular deviation experimentally monitored in step e is acceptable under the criteria defined in step c, and performing a selection from the group consisting of:
    accepting the said sequential system if said defined angular deviation criteria is met and proceeding to step g; and
    rejecting said sequential system and repeating step e with another selected pairing of similar elements if said defined angular deviation criteria is not met;
  g) if practice of step f results in accepting said sequential system, proceeding to determine if a laterally offset exists between the beam entered to the first element and that exiting the second element, and if so performing at least one selection from the group consisting of:
    changing the relative orientation of said selected elements with respect to one another; and
    rotating said system of the two selected elements as said unit about an axis not parallel to the beam of electromagnetic radiation;
until said lateral offset entered to said beam of electromagnetic radiation is determined to be acceptable under the criteria defined in step c;
  h) optionally experimentally re-checking if the angular deviation entered to said beam of electromagnetic radiation is still acceptable after practice of step g; and accepting said sequential system only if both the angular deviation and lateral offset entered to said beam of electromagnetic radiation are then acceptable under the criteria of step c;
  i) said method further comprising:
    i1) providing a containment system with provision for receiving selected elements thereinto in a desired relationship with respect to one another;
    i2) placing said selected elements into said containment system.

7. A method as in claim 6 in which said containment system is characterized by:
  an outer enclosure which separates an outer environment from the enclosed inner volume in which is present said provision for receiving selected elements thereinto in a desired relationship with respect to one another therewithin;
  said outer enclosure further comprising means for flowing purging gas into and out of said enclosed inner volume such that the inner volume is caused to contain a gas in contact with the outer surfaces of said selected elements caused to be present therein;
and in which said method further comprises:
  j) flowing a gas into said enclosed inner volume through said means for flowing purging gas into said enclosed inner volume, such that some amount thereof passes through said inner volume and out of said means for flowing gas out of said inner volume;
  k) optionally sealing said means for flowing purging gas into and out of said enclosed inner volume such that outside environment can not thereafter enter into said inner volume;
to the end that the inner volume is caused to contain said gas which is in contact with the outer surfaces of said selected elements caused to be present therein.

8. A method as in claim 6, in which the elements paired by said computer program in step d are paired as neither of them was experimentally determined to enter significant angular deviation to a beam of electromagnetic radiation in step b.

9. A method as in claim 6, in which the elements paired by said computer program in step d are paired as each of them was experimentally determined to enter angular deviation to a beam of electromagnetic radiation in step b, but in an offsetting manner.

10. A method as in claim 6, wherein said similar elements provide at least two sides, either of which is oriented to serve as the side into which a beam of electromagnetic radiation is input, and in which the step b practice of experimentally determining and recording data describing measured angular deviation entered to a beam of electromagnetic radiation by each of said multiplicity of similar elements individually is performed for each such orientation, and in which all recorded data is considered in step e.

11. A method as in claim 6 which said method further comprises determining, and placing in order, the relatively best pairings of similar elements by a method selected from the group consisting of:
  using results from applying said computer program in step d to data recorded in step b to identify pairings of similar elements which in sequence provide the least beam angular deviation; and
  recording experimental data determined in step e and applying said data to identify pairings of similar elements which in sequence provide the least beam angular deviation.

12. A method as in claim 11 which optionally further comprises defining a cut-off criteria point as regards beam angular deviation, and rejecting pairings which do not meet said cut-off criteria.

13. A method as in claim 6, in which step a involves providing parallelogram shaped rhombs and step e involves selecting two sequential parallelogram shaped rhombs as elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween, said two parallelogram shaped rhombs being oriented with their first and third sides being substantially parallel to one another, wherein "substantially parallel to one another" means that said third (RS3) side of said first and first (RS1) side of the second of said parallelogram shaped rhombs are offset from being parallel to one another by no more than about +/−ten (10) degrees;

such that a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof.

14. A method as in claim 13, in which step c involves selecting two sequential parallelogram shaped rhombs wherein the angles of the parallelogram shaped rhomb are nominally selected from the group consisting of:
36, 144, 36, and 144 degrees; and
45, 135, 45 and 135 degrees.

15. A method as in claim 13, in which step c involves selecting two sequential parallelogram shaped rhombs which are fabricated from fused silica.

16. A method as in claim 13, in which the selected two sequential parallelogram shaped rhombs are characterized by at least one of the second RS2 and forth RS4 sides of at least one of the parallelogram shaped rhombs having a coating thereupon which has a different refractive index than does the material from which said corresponding parallelogram shaped rhomb is comprised.

17. A method as in claim 16, in which step a involves providing a multiplicity of parallelogram shaped rhombs as elements and step e involves selecting two sequential parallelogram shaped rhombs as elements, each said rhomb having first RS1, second RS2, third RS3 and forth RS4 sides, said first RS1 and third RS3 sides being substantially parallel to one another and said second RS2 and forth RS4 sides being substantially parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween, said two parallelogram shaped rhombs being oriented with their first and third sides being substantially parallel to one another, wherein "substantially parallel to one another" means that said third (RS3) side of said first and first (RS1) side of the second of said parallelogram shaped rhombs are offset from being parallel to one another by no more than about +/−ten (10) degrees;

such that a beam of electromagnetic radiation caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof;

said system being characterized in that at least one of the second RS2 and forth RS4 sides of at least one of the parallelogram shaped rhombs has a coating thereupon which has a different refractive index than does the material from which said corresponding parallelogram shaped rhomb is comprised.

18. A method as in claim 17, in which step a involves providing two sequential parallelogram shaped rhombs wherein the angles of the parallelogram shaped rhomb are nominally selected from the group consisting of:
36, 144, 36, and 144 degrees; and
45, 135, 45 and 135 degrees.

19. A method as in claim 18, in which step a involves providing sequential parallelogram shaped rhombs which are fabricated from fused silica and the coating is $MgF_2$.

20. A method as in claim 6, in which step e involves selecting a system of sequential elements which are further characterized by at least one selection made from the group consisting of:

at least one of the sequential elements is mounted to a mechanism for translating and/or tilting the element, for the purpose of aligning the system such that the exiting beam is substantially angularly undeviated from said input beam;

at least one of the sequential elements has a coating upon a surface thereof at which internal reflection of a beam of electromagnetic radiation occurs, said coating having a different refractive index than does the material from which said corresponding element is comprised;

at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge W1 is rotated with respect to another W2 thereof and/or both wedges W1 W2 can be rotated simultaneously, for the purpose of aligning the system such that the output beam is substantially angularly undeviated from said input beam.

21. A system for introducing a relative phase retardation into orthogonally polarized components of an input electromagnetic beam entered thereinto, said system consisting of at least two sequential elements oriented with respect to one another such that said entered electromagnetic beam undergoes total internal reflection at least once in each of the at least two elements;

the sequence, orientation, geometry, and symmetry of the elements being such that the locus of an output beam exiting the system is substantially undeviated from the locus of the input beam;

said system being characterized in that:

two of said at least two sequential elements are parallelogram shaped rhombs, each said rhomb having first RS1, second RS2, third RS3 and forth RS4 sides, said first RS1 and third RS3 sides being parallel to one another and said second RS2 and forth RS4 sides being parallel to one another, said first RS1 and second RS2 sides of said first parallelogram shaped rhomb, and said second RS2 and third RS3 sides of said second parallelogram shaped rhomb meeting one another at angles greater than ninety degrees therebetween, and said second RS2 and third RS3 sides of said first parallelogram shaped rhomb and said first RS1 and second RS2 sides of said second parallelogram shaped rhomb meeting one another at angles less than ninety degrees therebetween, said at least two parallelogram shaped rhombs being oriented with their first and third sides being substantially parallel to one another;

such that an input beam of electromagnetic radiation is caused to enter the first RS1 side of one thereof, at a substantially normal angle thereto, then proceeds so that it internally reflects from said forth RS4 and second RS2 sides thereof, then exits said third RS3 side thereof in a direction such that it then enters the first RS1 side of the second thereof at a substantially normal angle thereto, then proceeds so that it internally reflects from said second RS2 parallelogram shaped rhomb and forth RS4 side thereof, then exits said third RS3 side thereof;

said system being further characterized in that at least one of the second RS2 and forth RS4 sides of at least one of the parallelogram shaped rhombs has a coating thereupon which has a different refractive index than does the material from which said corresponding parallelogram shaped rhomb is comprised;

wherein the at least two parallelogram shaped rhombs are fabricated from of fused silica and the coating on at least one thereof is 20-90 nm of lower refractive index MgF2.

22. A system as in claim 21, in which the angles of the at least two parallelogram shaped rhombs are 36, 144, 36, and 144 degrees, or 45, 135, 45 and 135 degrees.

23. A system as in claim 21, in which there are two parallelogram shaped rhombs oriented with the first and third sides of one thereof being substantially, but not exactly, parallel to the first and third sides of the other, such that an acute angle exists between:

the parallel first and third sides of one of one of the parallelogram shaped rhombs, and the parallel first and third sides of the other of the other thereof.

24. A system as in claim 23, in which the acute angle is nominally three degrees.

25. A system as in claim 21, in which one of said at least two parallelogram shaped rhombs is formed by a combination of two sequential elements (ra) and (rb), and the other thereof is formed by a combination of two sequential elements (rc) and (rd), said sequential elements, each being a right angle prisms having right angle sides adjacent to the right angle thereof and a side opposite the right angle thereof ha, hb, hc, hd respectively; said right angle prisms being oriented with respect to one another such that, as viewed in side elevation, the first ra right angle prism is positioned so that its side opposite the right angle thereof ha is facing downward and to the right, and so that directly above the first ra right angle prism is present the second right angle prism rb, which is oriented so that its side hb opposite the right angle thereof is facing upward and to the left, and so that directly to the right of the second rb right angle prism is the third rc right angle prism, which is oriented so that its side hc opposite the right angle thereof is facing upward and to the right, and so that directly below the third rc right angle prism is positioned the forth rd right angle prism, oriented so that its side hd opposite the right angle thereof is facing downward and to the left.

26. A system as in claim 21, wherein the locus of the input beam is oriented substantially perpendicularly to the first and third sides of each of the at least two parallelogram shaped rhombs.

27. A system as in claim 26, wherein the locus of the input beam is oriented substantially, but not exactly, perpendicularly to the first and third sides of each of the at least two parallelogram shaped rhombs.

28. A system as in claim 21 which is specifically characterized by at least one selection made from the group consisting of:

at least one of the sequential elements has a mechanism for translating and/or tilting the element, for the purpose of aligning the system such that the output beam is substantially undeviated from said input beam;

at least one of the sequential elements has a coating upon a surface thereof at which internal reflection of a beam of electromagnetic radiation occurs, said coating having a different refractive index than does the material from which said corresponding element is comprised;

at least one of the sequential elements has a coating upon a surface thereof through which a beam of electromagnetic radiation enters or exist, said coating having a different refractive index than does the material from which said corresponding element is comprised;

there is present an additional sequential multiple wedge system in said system for introducing a relative phase retardation into orthogonally polarized components of an electromagnetic beam, wherein one said wedge W1 can be rotated with respect to another W2 thereof and/or both wedges W1 W2 can be rotated simultaneously, for the purpose of aligning the system such that the output beam is substantially undeviated from said input beam.

29. A system as in claim 21, wherein the length to width aspect ratio of side RS2 to side RS1 in each of said parallelogram shaped rhombs is characterized by a selection from the group consisting of:

it is substantially less that 7.5; and it is about 1.0.

* * * * *